US007005255B2

(12) United States Patent
Kaddurah-Daouk et al.

(10) Patent No.: US 7,005,255 B2
(45) Date of Patent: Feb. 28, 2006

(54) METHODS FOR DRUG DISCOVERY, DISEASE TREATMENT, AND DIAGNOSIS USING METABOLOMICS

(75) Inventors: Rima Kaddurah-Daouk, Belmont, MA (US); Bruce Kristal, White Plains, NY (US)

(73) Assignees: Metabolon, Inc., Research Triangle Park, NC (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/757,616

(22) Filed: Jan. 13, 2004

(65) Prior Publication Data

US 2004/0146853 A1   Jul. 29, 2004

Related U.S. Application Data

(63) Continuation of application No. 09/835,119, filed on Apr. 13, 2001.

(60) Provisional application No. 60/239,340, filed on Oct. 11, 2000, provisional application No. 60/239,541, filed on Oct. 10, 2000, provisional application No. 60/197,117, filed on Apr. 14, 2000, provisional application No. 60/197,085, filed on Apr. 14, 2000.

(51) Int. Cl.
C12Q 1/00    (2006.01)
(52) U.S. Cl. .......................................................... 435/4
(58) Field of Classification Search .............. 435/7.21, 435/71; 424/9.1, 9.2; 436/518, 528
See application file for complete search history.

(56) References Cited

U.S. PATENT DOCUMENTS

| | | | |
|---|---|---|---|
| 4,511,659 A | 4/1985 | Matson | 436/150 |
| 4,863,873 A | 9/1989 | Matson | 436/63 |
| 5,104,639 A | 4/1992 | Matson | 424/2 |
| 5,541,310 A | 7/1996 | Ward et al. | 536/23.6 |
| 5,565,323 A | 10/1996 | Parker et al. | 435/6 |
| 5,824,467 A | 10/1998 | Mascarenhas | 435/4 |
| 5,871,712 A * | 2/1999 | Siman | 424/9.1 |
| 5,977,083 A | 11/1999 | Burcoglu | 514/44 |
| 6,004,755 A | 12/1999 | Wang | 435/6 |
| 6,087,090 A | 7/2000 | Mascarenhas | 435/4 |
| 6,168,933 B1 | 1/2001 | Kaser et al. | 435/91.1 |
| 6,190,858 B1 | 2/2001 | Persaud et al. | 435/4 |
| 6,194,217 B1 | 2/2001 | Matson | 436/63 |
| 6,210,970 B1 | 4/2001 | Matson | 436/64 |
| 6,218,117 B1 | 4/2001 | Herrnstadt et al. | 435/6 |
| 6,258,605 B1 | 7/2001 | Chace | 436/86 |
| 6,303,365 B1 | 10/2001 | Martin et al. | 435/252.3 |
| 6,319,668 B1 | 11/2001 | Nova et al. | 435/6 |
| 6,326,163 B1 | 12/2001 | Forssmann et al. | 435/24 |
| 6,326,164 B1 | 12/2001 | Rice et al. | 435/25 |
| 6,344,322 B1 | 2/2002 | Polyak et al. | 435/6 |
| 6,350,588 B1 | 2/2002 | Roth et al. | 435/34 |
| 6,376,210 B1 | 4/2002 | Yuan | 435/18 |
| 6,677,160 B1 | 1/2004 | Stockman et al. | 436/173 |
| 2002/0081626 A1 | 6/2002 | Kaddurah-Daouk et al. | 435/7.1 |

FOREIGN PATENT DOCUMENTS

| | | |
|---|---|---|
| WO | WO 86/03006 A1 | 5/1986 |
| WO | WO 92/13273 A1 | 8/1992 |
| WO | WO 93/10802 A1 | 6/1993 |
| WO | WO 96/23075 A1 | 8/1996 |
| WO | WO 98/29563 A1 | 7/1998 |
| WO | WO 98/37423 A1 | 8/1998 |
| WO | WO 99/27361 A1 | 6/1999 |
| WO | WO 99/37786 A2 | 7/1999 |
| WO | WO 99/37786 A3 | 7/1999 |
| WO | WO 99/38013 A2 | 7/1999 |
| WO | WO 99/44062 A1 | 9/1999 |
| WO | WO 99/50437 A1 | 10/1999 |
| WO | WO 00/07025 A2 | 2/2000 |
| WO | WO 00/07025 A3 | 2/2000 |
| WO | WO 00/09759 A1 | 2/2000 |
| WO | WO 00/51054 A1 | 8/2000 |
| WO | WO 00/55346 A2 | 9/2000 |
| WO | WO 00/55346 A3 | 9/2000 |
| WO | WO 00/65039 A2 | 11/2000 |
| WO | WO 00/65039 A3 | 11/2000 |
| WO | WO 00/65472 A1 | 11/2000 |
| WO | WO 01/00819 A1 | 1/2001 |
| WO | WO 01/09341 A2 | 2/2001 |
| WO | WO 01/09341 A3 | 2/2001 |
| WO | WO 01/09711 A2 | 2/2001 |
| WO | WO 01/18627 A2 | 3/2001 |
| WO | WO 01/18627 A3 | 3/2001 |
| WO | WO 01/23330 A2 | 4/2001 |
| WO | WO 01/23601 A2 | 4/2001 |
| WO | WO 01/23601 A3 | 4/2001 |
| WO | WO 01/26038 A1 | 4/2001 |
| WO | WO 01/40896 A2 | 6/2001 |
| WO | WO 01/40896 A3 | 6/2001 |

(Continued)

OTHER PUBLICATIONS

Niebroj-Dobosz, I, et al. 1999. Amino acids acting as transmitters in amyotrophic lateral sclerosis (ALS). Acta Neurol Scand vol. 100:6-11.*

(Continued)

Primary Examiner—Jeffrey Fredman
(74) Attorney, Agent, or Firm—Lahive & Cockfield, LLP; Elizabeth A. Hanley, Esq.; Cynthia M. Soroos, Esq.

(57) ABSTRACT

The small molecule profiles of cells are compared to identify small molecules which are modulated in altered states. Cellular small molecule libraries, methods of identifying tissue sources, methods for treating genetic and non-genetic diseases, and methods for predicting the efficacy of drugs are also discussed.

5 Claims, No Drawings

FOREIGN PATENT DOCUMENTS

| | | |
|---|---|---|
| WO | WO 01/55701 A1 | 8/2001 |
| WO | WO 01/55719 A2 | 8/2001 |
| WO | WO 01/57518 A2 | 8/2001 |
| WO | WO 01/69247 A2 | 9/2001 |
| WO | WO 01/69247 A3 | 9/2001 |
| WO | WO 01/73672 A1 | 10/2001 |
| WO | WO 01/79515 A2 | 10/2001 |
| WO | WO 01/84146 A2 | 11/2001 |
| WO | WO 01/84146 A3 | 11/2001 |
| WO | WO 02/04945 A1 | 1/2002 |
| WO | WO 02/04957 A2 | 1/2002 |
| WO | WO 02/09836 A2 | 2/2002 |
| WO | WO 02/22857 A2 | 3/2002 |
| WO | WO 02/33377 A2 | 4/2002 |
| WO | WO 02/052293 A1 | 7/2002 |
| WO | WO 02/085195 A2 | 10/2002 |
| WO | WO 02/085195 A3 | 10/2002 |
| WO | WO 02/086452 A2 | 10/2002 |
| WO | WO 02/086452 A3 | 10/2002 |
| WO | WO 02/086478 A2 | 10/2002 |
| WO | WO 02/086478 A3 | 10/2002 |
| WO | WO 02/086500 A2 | 10/2002 |
| WO | WO 02/086500 A3 | 10/2002 |
| WO | WO 02/086501 A2 | 10/2002 |
| WO | WO 02/086501 A3 | 10/2002 |
| WO | WO 02/086502 A2 | 10/2002 |

OTHER PUBLICATIONS

Rashed et al. Clinical Chemistry, vol. 43: 1129-1141, 1997.*

Nicholson, J.K. et al. 'Metabonomics': understanding the metabolic responses of living systems to pathophysiological stimuli via multivariate statistical analysis of biological NMR spectroscopic data. *Xenobiotica* Nov. 1999;29(11): 1181-9.

Trethewey, R.N. et al. Commentary. Metabolic profiling: a Rosetta Stone for genomics?*Current Opinion in Plant Biology* Mar. 1999;2:83-85.

"Biochemicals Organic Compounds and Diagnostic Reagents." In *Sigma Catalog "anonymous"* 1998, p. 253.

Brindle et al. "Rapid and noninvasive diagnosis of the presence and severity of coronary heart disease using H-NMR-based metabonomics." *Nat Med*.Dec. 2002;8(12): 1439-44.

Buchholz et al. "Metabolomics: quantification of intracellular metabolite dynamics." *Biomol Eng*.Jun. 2002;19(1):5-15.

Holmes et al. "Metabonomic characterization of genetic variations in toxicological and metabolic responses using probabilistic neural networks." *Chem Res Toxicol.* Feb. 2001;14(2): 182-91.

* cited by examiner

METHODS FOR DRUG DISCOVERY, DISEASE TREATMENT, AND DIAGNOSIS USING METABOLOMICS

RELATED APPLICATIONS

This application is a continuation of U.S. Ser. No. 09/835,119, filed Apr. 13, 2001, entitled "Methods for Drug Discovery, Disease Treatment, and Diagnosis Using Metabolomics", which claims priority to U.S. Provisional Application Ser. No. 60/239,340, entitled "Methods for Drug Discovery, Disease Treatment, and Diagnosis Using Metabolomics" filed on Oct. 11, 2000; U.S. Provisional Application Ser. No. 60/239,541, entitled "Methods for Drug Discovery, Disease Treatment, and Diagnosis Using Metabolomics" filed on Oct. 10, 2000; U.S. Provisional Application Ser. No. 60/197,117, entitled "Small Molecule Profiles of Cells and Methods Of Use Thereof," filed on Apr. 14, 2000; and U.S. Provisional Application Ser. No. 60/197,085, entitled "Cellular Small Molecule Libraries," filed on Apr. 14, 2000. The entire contents of each of the aforementioned applications are hereby incorporated herein by reference.

BACKGROUND OF INVENTION

Living organisms are autonomous chemical systems which include diverse sets of small molecules. Small molecules found in living systems include, for example, sugars, fatty acids, amino acids, nucleotides, and intermediates of metabolic and signaling pathways. Sugars are a primary source of chemical energy for cells. The cells break the sugars down through a series of oxidative reactions to small sugar derivatives and, ultimately, $CO_2$ and $H_2O$. Fatty acids used for both energy storage and as major components of cellular membranes. Amino acids are the building blocks of proteins. Nucleotides are involved in intracellular signaling, energy transfer, and as the monomers of the information macromolecules, RNA and DNA.

The cellular small molecules are, generally, composed of six elements (C, H, N, O, P, S). If water is excluded, carbon compounds comprise a large majority of the cellular small molecules. The cellular small molecules repeatedly use certain distinctive chemical groups, such as methyl ($CH_3$), carboxyl (COOH) and amino ($NH_2$) groups.

Generally, most cellular small molecules are synthesized from and broken down to the same basic compounds. Synthesis and metabolism occurs through sequences of controlled chemical reactions, catalyzed by enzymes. Most of the metabolic reactions of the cell occur in the cytoplasm, which contains many distinctive organelles. For example, the mitochondria are responsible for respiration and energy production. Mitochondria are the "power plants" of eukaryotic cells, harnessing energy contained by combining oxygen with metabolites to make ATP. Other organelles of the cell include the Golgi apparatus, a system of stacked, membrane bound, flattened sacs involved in modifying, sorting and packaging of macromolecules for secretion or for delivery to other organelles. The endoplasmic reticulum (ER) is a series of flattened sheets, sacks, and tubes of membrane extending throughout the cytoplasm of eukaryotic cells. The ER membrane is in structural continuity with the outer membrane of the nuclear envelope and specializes in the synthesis and transport of lipids and membrane proteins.

SUMMARY OF INVENTION

In recent years, scientists have attempted to study cells and living systems through the cataloging of the entire genome of an organism (e.g., genomics). Genomics is a powerful tool, useful for identifying and interrogating the entire inventory of genes of a living system. Recently, scientists have also attempted to identify and interrogate all the proteins present in the cell or organism through proteomics. However, most pharmaceutical companies who study genomics and proteomics realize that many of their anticipated products are not proteins nor genes but small molecules.

For example, once a novel gene or target is discovered by genomics, the investigators must first validate the target using expensive and time consuming procedures which are far removed from the actual disease state. Examples of typical validation procedures include expression profiling, generating knock-out mice or transgenic mice, in situ hybridization, etc. Once a target is validated, the investigators typically screen enormous random small molecule libraries to identify molecules which interact with the protein targets. The identified small molecules typically optimized through chemical synthesis in order to obtain a marketable product.

The invention pertains, at least in part, to the generation and the analysis of small molecule profiles of cells, cellular compartments, and specific organelles (e.g., mitochondria, Golgi, endoplasmic reticulum, cytoplasm, nucleus, etc.) Small molecule profiles allow for the identification and interrogation of inventories of small molecules (e.g., the metabolome) to find, for example, disease-relevant small molecules as well as potential targets for drug design.

Small molecule profiles of cells and organelles can be used directly to identify drug candidates. Unlike genomics, small molecule profiling can either eliminate entirely or accelerate the process of identifying genes and proteins associated with a disease state. In one embodiment of the invention, the methods of the invention include, for example, comparing small molecule profiles of diseased cells, cellular compartments, and organelles to standard profiles of a healthy cells, cellular compartments, and organelles. Therefore, if a particular diseased cell, cellular compartment, or organelle was found to be deficient in a particular compound, the deficiency may be overcome by simply administering the compound or an analogue thereof. Metabolomics offers a new route to the identification of potentially therapeutic agents and targets.

Metabolomics eliminates much of the guess work surrounding genomics. For example, small molecule profiling allows one to investigate the very biochempathway (e.g., cellular metabolites) involved in the disease state by comparing small molecule profiles of cells, cellular compartments, or organelles with those of cells, cellular compartments, or organelles treated with toxins, chemical agents or other therapeutic agent (or derived from an organism treated with the agent or drug).

The invention also includes methods for identifying potential cell drug targets (e.g., cellular components which interact with the labeled small molecules). This method is particularly useful because it can identify components which are known to interact with disease relevant small molecules. Therefore, targets identified through this method are "prevalidated," and some of the guess work surrounding the choice of target is eliminated. In a further embodiment, this method can be used in conjunction with conventional genomics as a further validation step to identify targets for further research.

Unlike genomics, small molecule profiling is not limited to disease states with a genetic component. Many disease states are not genetically determined and genomics offers little to those suffering or at risk of suffering from non-genetic linked disease states. Therefore, there is a need for a comprehensive method to study the effects of nongenetic factors on cells and living systems.

Small molecule profiling of cells or organelles can be used to study both genetic and non-genetically linked disease states. For example, methods of the invention can be used to identifying small molecules associated with, for example, body weight disorders, central nervous system disorders, cardiovascular disorders, immunological disorders, oncological disorders, etc.

In addition, metabolomics can be used in tandem with genomics and/or proteomics. For example, small molecule profiles can be used to identify small molecules regulated, modulated, or associated with genetic modification or alterations of cells, both engineered and naturally occurring.

In addition, metabolomics can also be applied to the field of predictive medicine. For example, the invention pertains to diagnostic assays, prognostic assays, pharmacometabolomics, and the monitoring clinical trails which are used for prognostic (predictive) purposes to treat an individual prophylactically, based on an individual's "metaboprint." Unlike pharmacogenetics, which is limited to genetic factors, pharmacometabolomics is able to predict an individual's response to a drug based not only on genetic factors, but also non-genetic factors, such as other drugs in the patient's body, the patient's current state of health, etc. Pharmacometabolomics allows for the use of a subject's small molecule profile (or "metaboprint") to deliver the right drug to the right patient. Subjects respond differently to drugs based on their small molecule profiles.

The small molecule profiling of cells, cellular compartments, and/or particular organelles of the present invention can also be used to identify individuals from minute biological samples. The method includes taking one or more samples from a subject and determining the small molecule profiles of the samples; taking a sample from a unknown source and determining its small molecule profile; and comparing the two small molecule profiles to determine whether the small molecule profiles are from the same individual.

The invention also pertains, for example, to pharmaceutical compositions comprised of compounds identified by the methods of the invention and a pharmaceutical carrier.

In another embodiment of the invention, the invention includes a method for the identification of insecticides, herbicides, and other compositions for agricultural use.

DETAILED DESCRIPTION OF THE INVENTION

1. Small Molecule Profiles of Cells, Cellular Compartments, and Organelles

The invention pertains, at least in part, to the generation of small molecule profiles of samples, cells, and cellular compartments. Small molecule profiles "fingerprint" the cell or cellular compartment and identify the presence, absence or relative quantity of small molecules. The small molecule profiles of the cells or cellular compartments may be obtained through, for example, a single technique or a combination of techniques for separating and/or identifying small molecules known in the art. Examples of separation and analytical techniques which can be used to separate and identify the compounds of the small molecule profiles include: HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. Preferably, the methods of the invention detect both electrically neutral as well as electrochemically active compounds. Detection and analytical techniques can be arranged in parallel to optimize the number of molecules identified.

The term "sample" include cellular extracts from which a small molecule profile of the extract can be obtained. In one embodiment, the samples are substantially free of macromolecules (e.g., large proteins and polynucleotides with molecular weights of greater than 10,000). The sample may be obtained from the entire cell or from specific cellular compartments. Examples of specific cellular compartments include the cytoplasm, the mitochondria, the Golgi apparatus, the endoplasmic reticulum, the nucleus, the chloroplasts, the cytosol, etc. The term "samples" includes both isolated small molecules and mixtures of small molecules.

The term "cells" includes prokaryotic cells, eukaryotic cells, yeast cells, bacterial cells, plant cells, animal cells, such as, reptilian cells, bird cells, fish cells, mammalian cells. Preferred cells include those derived from humans, dogs, cats, horses, cattle, sheep, pigs, llamas, gerbils, squirrels, goats, bears, chimpanzees, mice, rats, rabbits, etc. The term cells includes transgenic cells from cultures or from transgenic organisms. The cells may be from a specific tissue, body fluid, organ (e.g., brain tissue, nervous tissue, muscle tissue, retina tissue, kidney tissue, liver tissue, etc.), or any derivative fraction thereof. The term includes healthy cells, transgenic cells, cells affected by internal or exterior stimuli, cells suffering from a disease state or a disorder, cells undergoing transition (e.g., mitosis, meiosis, apoptosis, etc.), etc.

In a further embodiment, the samples are obtained from a specific cellular compartment. The term "cellular compartment" includes organelles (such as mitochondria, Golgi apparatus, centrioles, chloroplasts), the nucleus, the cytoplasm (optionally including the organelles), and other cellular regions capable of being isolated. In one embodiment, the cellular compartment is the entire cell.

The analysis of a particular cellular compartment has many advantages over analysis of whole cells, whole cell lysates, body fluids, etc. For example, often the mechanism of action of a drug, a toxic compound, etc. is directed to a specific cellular function, such as, for example, the electron transport chain in the mitochondria, nucleic acid replication in the nucleus, etc. By isolating the specific cellular compartment or organelle (e.g., mitochondria, nuclei, Golgi apparatus, endoplasmic reticulum, ribosomes, etc.), it is possible to narrow the focus of the profile to small molecules involved in the relevant pathway. Previously, metabolome studies have been complicated by the large number of chemical species present in a given sample. By narrowing the scope of the study to the particular organelle, researchers will be able to study the pathway of interest in more detail without irrelevant molecules present in interstitial fluid, blood, spinal fluid, saliva, etc.

The term "small molecules" includes organic and inorganic molecules which are present in the cell, cellular compartment, or organelle. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell. In one embodiment, the small molecules of the invention are isolated.

The term "metabolome" includes all of the small molecules present in a given organism. The metabolome includes both metabolites as well as products of catabolism. In one embodiment, the invention pertains to a small molecule profile of the entire metabolome of a species. In another embodiment, the invention pertains to a computer database (as described below) of the entire metabolome of a species, e.g., an animal, e.g., a mammal, e.g., a mouse, rat, rabbit, pig, cow, horse, dog, cat, bear, monkey, and, preferably, a human. In another embodiment, the invention pertains to a small molecule library of the entire metabolome of an organism (as described below), e.g., a mammal, e.g., a mouse, rat, rabbit, pig, cow, horse, dog, cat, bear, monkey, and, preferably, a human.

The language "small molecule profile" includes the inventory of small molecules in tangible form within a targeted cell, tissue, organ, organism, or any derivative fraction thereof, e.g., cellular compartment, that is necessary and/or sufficient to provide information to a user for its intended use within the methods described herein. The inventory would include the quantity and/or type of small molecules present. The ordinarily skilled artisan would know that the information which is necessary and/or sufficient will vary depending on the intended use of the "small molecule profile." For example, the "small molecule profile," can be determined using a single technique for an intended use but may require the use of several different techniques for another intended use depending on such factors as the disease state involved, the types of small molecules present in a particular targeted cellular compartment, the cellular compartment being assayed per se., etc.

The relevant information in a "small molecule profile" also may vary depending on the intended use of the compiled information, e.g. spectra. For example for some intended uses, the amounts of a particular small molecule or a particular class of small molecules may be relevant, but for other uses the distribution of types of small molecules may be relevant.

The ordinarily skilled artisan would be able to determine the appropriate "small molecule profiles" for each method described herein by comparing small molecule profiles from diseased and/or test subjects with standard and/or healthy subjects. These comparisons can be made by individuals, e.g., visually, or can be made using software designed to make such comparisons, e.g., a software program may provide a secondary output which provides useful information to a user. For example, a software program can be used to confirm a profile or can be used to provide a readout when a comparison between profiles is not possible with a "naked eye". The selection of an appropriate software program, e.g., a pattern recognition software program, is within the ordinary skill of the art. An example of such a program is Pirouette. It should be noted that the comparison of the profiles can be done both quantitatively and qualitatively.

The small molecule profiles can be obtained from an organism suffering from a disease state, genetic alteration, or any of the models discussed in more detail below. In one embodiment, the small molecule profile of an organism is determined by using HPLC (Kristal, et al. *Anal. Biochem.* 263:18–25 (1998)), thin layer chromatography (TLC), or electrochemical separation techniques (see, WO 99/27361, WO 92/13273, U.S. Pat. Nos. 5,290,420, 5,284,567, 5,104,639, 4,863,873, and U.S. Pat. No. RE32,920). Other techniques for determining the presence of small molecules or determining the identity of small molecules of the cell are also included, such as refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. The small molecule profiles of the invention may also be referred to as "metaboprints." The exact combination of techniques used to determine the small molecule profiles can be determined by In one embodiment, the invention pertains to small molecule profiles generated by several methods, e.g., HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art.

The methods of the invention have several advantages over methods which rely only on a single mode of analysis, such as electrochemical separation. While electrochemical separation works only for "electrochemically" active compounds, it does not effectively separate neutral molecules. The invention here relates to the use in tandem and in parallel of a multitude of these detectors. This will result in the identification of a more comprehensive database. The detectors are usually attached to the HPLC columns where they can detect and emit a response due to the eluting sample and subsequently signal a peak on a chromatogram. The bandwidth and height of the peaks may usually be adjusted using the coarse and fine tuning controls and the detection and sensitivity parameters may also be controlled. There are many detectors that can be used with the HPLC. Some detectors which can be used in the methods of the invention include: Refractive Index (RI), Ultra-Violet (UV), Fluorescent, Radiochemical, Electrochemical, Near-InfraRed (Near-IR), Mass Spectroscopy (MS), Nuclear Magnetic Resonance (NMR), Light Scattering (LS) among others.

The methods of the invention can be used to detect both electrochemically active molecules as well as electrochemically neutral molecules. In a further embodiment, the invention pertains to methods which detect about 50% or more, about 60% or more, about 70% or more, about 75% or more, about 77.5% or more, about 80% or more, about 82.5% or more, about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more of the small molecules of a cellular compartment (e.g., mitochondria, chloroplast, endoplasmic reticulum, nuclei, Golgi apparatus, cytosol, etc.).

In one embodiment, HPLC columns equipped with coulometric array technology can be used to analyze the samples, separate the compounds, and/or create a small molecule profiles of the samples. Such HPLC columns have been used extensively in the past for serum, urine and tissue analysis and are suitable for small molecule analysis (Acworth et al., 300; Beal et al., *J Neurochem.* 55, 1327–1339, 1990; Matson et al., *Life Sci.* 41, 905–908, 1987; Matson et al., *Basic, Clinical and Therapeutic Aspects of Alzheimer's and Parkinson's Diseases*, vol II, pp. 513–516, Plenum, N.Y. 1990; LeWitt et al., *Neurology* 42, 2111–2117, 1992; Milbury et al., *J. Wildlife Manag.*, 1998; Ogawa et al., *Neurology* 42, 1702–1706, 1992; Beal et al., *J. Neurol. Sci* 108, 80–87, 1992, Matson et al., *Clin. Chem.* 30, 1477–1488, 1984; Milbury et al., *Coulometric Electrode Array Detectors for HPLC*, pp. 125–141, VSP International Science Publication; Acworth et al., *Am. Lab* 28, 33–38, 1996). HPLC columns equipped with coulometric arrays have been used for the simultaneous analysis of the majority of low-molecule weight, redox-active compounds in mitochondria. (*Anal. Biochem.* 263, 18–25, 1998).

For the detection and characterization of the small molecules in an effort to create a comprehensive small molecule profiles, a multitude of detection methods can be used. These methods are described in more detail below.

A. Mass Spectroscopy (MS) Detectors:

The sample compound or molecule is ionized, it is passed through a mass analyzer, and the ion current is detected. There various methods for ionization. Examples of these methods of ionization include electron impact (EI) where an electric current or beam created under high electric potential is used to ionize the sample migrating off the column, chemical ionization utilizes ionized gas to remove electrons from the compounds eluting from the column; and fast atom bombardment where Xenon atoms are propelled at high speed in order to ionize the eluents from the column.

B. Pyrolysis Mass Spectrometry:

Pyrolysis is the thermal degradation of complex material in an inert atmosphere or vacuum. It causes molecules to cleave at their weakest points to produce smaller, volatile fragments called pyrolysate (Irwin 1982). Curie-point pyrolysis is a particularly reproducible and straightforward version of the technique, in which the sample, dried onto an appropriate metal is rapidly heated to the Curie-point of the metal. A mass spectrometer can then be used to separate the components of the pyrolysate on the basis of their mass-to-charge ratio to produce a pyrolysis mass spectrum (Meuzelaar et al 1982) which can then be used as a "chemical profile" or fingerprint of the complex material analyzed. The combined technique is known as pyrolysis mass spectrometry (PyMS).

C. Nuclear Magnetic Resonance (NMR) Detectors:

Certain nuclei with odd-numbered masses, including H and $^{13}$C, spin about an axis in a random fashion. When they are placed between poles of a strong magnet, the spins are aligned either parallel or anti-parallel to the magnetic field, with parallel orientation favored since it is slightly lower energy. The nuclei are then irradiated with electromagnetic radiation which is absorbed and places the parallel nuclei into a higher energy state where they become in resonance with radiation. Different spectra will be produced depending on the location of the H or $^{13}$C and on adjacent molecules or elements in the compound because all nuclei in molecules are surrounded by electron clouds which change the encompassing magnetic field and thereby alter the absorption frequency.

D. Refractive Index (RI):

In this method, detectors measure the ability of samples to bend or refract light. This property for each compound is called refractive index. For most RI detectors, light proceeds through a bi-modular flow to a photodetector. One channel of the flow-cell directs the mobile phase passing through the column while the other directs only the other directs only the mobile phase. Detection occurs when the light is bent due to samples eluting from the column, and is read as a disparity between the two channels. Laser based RI detectors have also become available.

E. Ultra-Violet (UV) Detectors:

In this method, detectors measure the ability of a sample to absorb light. This could be accomplished at a fixed wavelength usually 254 nm, or at variable wavelengths where one wavelength is measured at a time and a wide range is covered, alternatively Diode Array are capable of measuring a spectrum of wavelengths simultaneously. Sensitivity is in the $10^{-8}$ to $10^{-9}$ gm/ml range. Laser based absorbance or Fourier Transform methods have also been developed.

F. Fluorescent Detectors:

This method measure the ability of a compound to absorb then re-emit light at given wavelengths. Each compound has a characteristic fluorescence. Each compound has a characteristic fluorescence. The excitation source passes through the flow-cell to a photodetector while a monochromator measures the emission wavelengths. Sensitivity is in the $10^{-9}$ to $10^{-11}$ gm/ml. Laser based fluorescence detectors are also available.

G. Radiochemical Detection:

This method involves the use of radiolabeled material, for example, tritium ($^3$H) or carbon 14 ($^{14}$C). It operates by detection of fluorescence associated with beta-particle ionization, and it is most popular in metabolite research. The detector types include homogeneous method where addition of scintillation fluid to column effluent causes fluorescence, or heterogeneous detection where lithium silicate and fluorescence by caused by beta-particle emission interact with the detector cell. Sensitivity is $10^{-9}$ to $10^{-10}$ gm/ml.

H. Electrochemical Detection:

Detectors measure compounds that undergo oxidation or reduction reactions. Usually accomplished by measuring gains or loss of electrons from migration samples as they pass between electrodes at a given difference in electrical potential. Sensitivity of $10^{-12}$ to $10^{-13}$ gms/ml.

I. Light Scattering (LS) Detectors:

This method involves a source which emits a parallel beam of light. The beam of light strikes particles in solution, and some light is then reflected, absorbed, transmitted, or scattered. Two forms of LS detection may be used to measure transmission and scattering.

Nephelometry, defined as the measurement of light scattered by a particular solution. This method enables the detection of the portion of light scattered at a multitude of angles. The sensitivity depends on the absence of background light or scatter since the detection occurs at a black or null background. Turbidimetry, defined as the measure of the reduction of light transmitted due to particles in solution. It measures the light scatter as a decrease in the light that is transmitted through particulate solution. Therefore, it quantifies the residual light transmitted. Sensitivity of this method depends on the sensitivity of the machine employed, which can range from a simple spectrophotometer to a sophisticated discrete analyzer. Thus, the measurement of a decrease in transmitted light from a large signal of transmitted light is limited to the photometric accuracy and limitations of the instrument employed.

Near Infrared scattering detectors operate by scanning compounds in a spectrum from 700–1100 nm. Stretching and bending vibrations of particular chemical bonds in each molecule are detected at certain wavelengths. This is a fast growing method which offers several advantages; speed, simplicity of preparation of sample, multiple analyses from single spectrum and nonconsumption of the sample (McClure, 1994).

J. Fourier Transform Infrared Spectroscopy (FT-IR):

This method measures dominantly vibrations of functional groups and highly polar bonds. The generated fingerprints are made up of the vibrational features of all the sample components (Griffiths 1986). FT-IR spectrometers record the interaction of IR radiation with experimental samples, measuring the frequencies at which the sample absorbs the radiation and the intensities of the absorptions. Determining these frequencies allows identification of the samples chemical makeup, since chemical functional groups are known to absorb light at specific frequencies. Both quantitative and qualitative analysis are possible using the FT-IR detection method.

K. Dispersive Raman Spectroscopy:

Dispersive Raman Spectroscopy is a vibrational signature of a molecule or complex system. The origin of dispersive raman spectroscopy lies in the inelastic collisions between the molecules composing say the liquid and photons, which are the particles of light composing a light beam. The collision between the molecules and the photons leads to an exchange of energy with consequent change in energy and hence wavelength of the photon.

To create a small molecule profile (or "Metaboprint") organs, cells, cellular compartments, or organelles are homogenized in standard ways know for those skilled in the art. Different fractionation procedures can be used to enrich the fractions for small molecules. The small molecules obtained will then be passed over several fractionation columns. The fractionation columns will employ a variety of detectors used in tandem or parallel to generate the small molecule profile for the organ, cell, cellular compartment, or organelle.

For example, to generate a small molecule profile of water soluble molecules, the cell, cellular compartment, or organelle extracts will be fractionated on HPLC columns with a water soluble array. The water soluble small molecules can then be detected using fluorescence or UV detectors to generate the small molecule profiles. Alternatively, electrochemical detectors can be used with diads to pick up redox active compounds and the absorbance of active compounds. For generating detecting non water soluble molecules, hydrophobic columns can also be used to generate small molecule profiles. In addition, gas chromatography combined with mass spectroscopy, liquid chromatography combined with mass spectroscopy, MALDI combined with mass spectroscopy, ion spray spectroscopy combined with mass spectroscopy, capillary electrophoresis, NMR and IR detection are among the many other combinations of separation and detection tools which can be used to generate small molecule profiles.

These small molecule profiles (or "metaboprints") will be able to define and characterize organs, cells, cellular compartments, and organelles by their small molecule content in both health and disease states. The information generated by the small molecule profiles will be both qualitative and quantitative.

2. Methods of Identification of Disease-Relevant Small Molecules

In another embodiment, the invention includes a method of identifying disease-relevant small molecules. The method includes comparing small molecule profiles of diseased cells, cellular compartments, or organelles to a standard profile of a healthy cell, cellular compartment, or organelle. The method also involves identifying the small molecules which are present in aberrant amounts in the diseased small molecule profile. The small molecules present in aberrant amounts in the diseased cells are "disease-relevant small molecules."

The language "disease-relevant small molecules" includes both small molecules present in aberrant amount in diseased small molecule profiles and, in addition, small molecules which are potentially involved in disease initiation, progression or prediction. The term also includes small molecules which are identified using the assays for particular diseases given below, as well as, compounds which are identified as being associated with particular genes of interest, also given below. The term also may include small molecules which when modulated, result in the lessening or curing of at least one symptom of a disease. The disease relevant small molecules are ideal drug candidates in the screening assays discussed elsewhere in the application.

For example, identified disease relevant small molecules may be screened using in vitro or in vivo assays known in the art to determine biological activity. The biological activity of disease relevant small molecules can also be pinpointed by using screening assays against protein targets which have been implicated in the disease state. In another embodiment, the biological activity of disease relevant small molecules can be determined using cell-based assays, e.g., tumor cell assays (Lillie et al. *Cancer Res.* 53(13):3172–8 (1993)). The disease relevant small molecules can also be tested for neuronal protection activity by exposing primary or cultured neurons to the compounds and toxic agents, such as glutamate, and identifying the compounds which protect the neurons from death. Animal models can also be used to further identify the biological activity of disease relevant small molecules. For example, animal models of Huntington's Disease, Parkinson's disease, and ALS can be used to identify small molecules useful as neuroprotective agents. (Kilvenyi, *Nature Med.* 5:347–350 (1999); Mathews et al, *Experimental Neurology* 157:142–149 (1999)). In a further embodiment, the disease relevant small molecules can be chemically modified to further enhance their pharmaceutical or nutriceutical properties.

The term "disease" or "disease state" includes all disease which result or could potentially cause a change of the small molecule profile of a cell, cellular compartment, or organelle in an organism afflicted with said disease. Examples of diseases include metabolic diseases (e.g., obesity, cachexia, diabetes, anorexia, etc.), cardiovascular diseases (e.g., atherosclerosis, ischemia/reperfusion, hypertension, restenosis, arterial inflammation, etc.), immunological disorders (e.g., chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy, etc.), nervous system disorders (e.g., neuropathies, Alzheimer disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, aging, dementia, peripheral nervous system diseases and mental disorders such as depression and schizophrenia, etc.), oncological disorders (e.g., leukemia, brain cancer, pancreatic cancer, prostate cancer, liver cancer, stomach cancer, colon cancer, throat cancer, breast cancer, ovarian cancer, skin cancer, melanoma, etc.). The term also include disorders which result from oxidative stress.

The language "aberrant levels" includes any level, amount, or concentration of a small molecule in a cell, cellular compartment, or organelle which is different from the level of the small molecule of a standard sample.

The term "standard profile" includes profiles derived from healthy cells, advantageously from a similar origin as the source. In one embodiment, the standard profile is an average of many samples of a certain cell type and/or a certain cellular compartment. In another embodiment, the standard profile may be derived from a patient prior to the onset of the disease state or from cells not affected by the disease state. Or, in another embodiment the standard profile can be an average of the profiles obtained from numerous sources, e.g., the standard profile may be an average of small molecule profiles obtained from 2 or more subjects. The standard profile can be a small molecule profile of a certain cellular compartment or from a certain subset of cells. In one embodiment, the invention pertains to the standard profile of healthy cells. Advantageously, the small molecules with aberrant levels in the sample are identified, e.g., HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. In one embodiment, the small molecule profile of the sample, cell, or cellular compartment, is compared to the standard profile by using subtracting one profile from the other. The compounds which are present in aberrant amounts can then be used in drug design to identify deregulated cellular components. Standard profiles can also be made of the effects of certain agents (e.g., drugs, therapeutic agents, toxins, etc.) on both healthy and diseased cells (e.g., cells diseased with the type of disease treated by the therapeutic agent).

Furthermore the language "standard profile" includes information regarding the small molecules of the profile that is necessary and/or sufficient to provide information to a user for its intended use within the methods described herein. The standard profile would include the quantity and/or type of small molecules present. The ordinarily skilled artisan would know that the information which is necessary and/or sufficient will vary depending on the intended use of the "standard profile." For example, the "standard profile," can be determined using a single technique for an intended use but may require the use of several different techniques for another intended use depending on such factors as the types of small molecules present in a particular targeted cellular compartment, the cellular compartment being assayed per se., etc.

The relevant information in a "standard profile" also may vary depending on the intended use of the compiled information, e.g. spectra. For example for some intended uses, the amounts of a particular small molecule or a particular class of small molecules of the standard profile may be relevant, but for other uses the distribution of types of small molecules small molecules of the standard profile may be relevant.

Furthermore, comparison of the standard profiles to profiles from diseased cells can be used to identify small molecules deregulated in the disease state. The small molecules identified can be used to guide the drug discovery effort. For example, the small molecules present in aberrant levels in the sample cells, can be identified and used as pharmaceutical or nutricutical agents. For example, if a patient is suffering from a disease state associated with a aberrantly low level of a certain compound, the compound or a precursor thereof may be tested in an assay that mimics the disease state. In another embodiment, the small molecules present in aberrant amounts may be used as targets for drug design to develop agents with enhanced activity, e.g., enhanced activity to treat the disease state associated with the aberrant levels of the small molecule. Additionally libraries of small molecules based on the structures of the small molecules present in aberrant amounts can be used to develop more potent therapeutics. The cellular targets and pathways could also be used to guide drug design.

In a further embodiment, the invention pertains to a method for treating a patient with a deficiency in certain disease relevant small molecules. The method includes obtaining cells from the patient, obtaining the small molecule profile of either a particular organelle (e.g., mitochondria, nucleus, cytoplasm, Golgi apparatus, endoplasmic reticulum, etc.) or a cell, comparing the small molecule profile with a standard profile, determining a deficiency in the patient's small molecule profile of a certain disease relevant small molecule, and administering the disease relevant small molecule to the patient.

In a further embodiment, the invention features diagnostic assays for the detection of disease states. For example, the method includes identifying a small molecule which is present in aberrant amounts in a particular disease state, e.g., by comparing standard profiles of diseased cells or cellular compartments with healthy cells or cellular compartments to identify compounds which are present in aberrant amounts in the diseased cell or cellular compartment. The method also involves designing a reagent that specifically reacts with the compound present in aberrant amounts to indicate the presence or absence of the compound, and therefore, the presence or the absence of the disease. The invention also pertains to kits which include the reagent and instructions for its use to diagnose the disease.

3. Methods of Identifying the Effect of Chemical Agents on Small Molecule Profiles of Cells, Cellular Compartments and Organelles In another aspect, the invention pertains to the comparison of small molecule profiles of cells, cellular compartments, or organelles with those of cells, cellular compartments, or organelles treated with toxins, chemical agents or therapeutic agent (or derived from an organism treated with the agent or drug). In one embodiment, the cells, cellular compartments, or organelles are diseased (or derived from a diseased organism) and are treated with a therapeutic agent which is known to modify or treat that disease. For example, the small molecule profile of a cell treated with a therapeutic agent, chemical agent, or toxin, can be compared the small molecule profile of a normal cell, e.g., a healthy cell of similar lineage, or a diseased cell of similar lineage which was not treated with the therapeutic agent, chemical agent, or toxin. Examples of toxins include bacterial toxins such as endotoxins and exotoxins, such as cholera toxin, diptheria toxin, verotoxin, enterotoxin, etc. In a further embodiment, the cells are genetically altered.

In addition, subtraction profiles can be obtained by subtracting the non-treated profile or a standard profile with the small molecule profile from a treated cell, cellular compartment, or organelle. The subtraction profiles can then be used to identify certain small molecules the presence or the absence of which may indicate the efficacy or the toxicity of the compound. The subtraction profiles can be made using, for example, computer programs known to those of skill in the art, e.g., pattern recognition software program. An example of such a program is Pirouette. It should be noted that the comparison of the profiles can be done both quantitatively and qualitatively.

In a further embodiment, the invention pertains to certain small molecules which indicate the efficacy or the toxicity of the compound. The invention also applies to assays which can be developed to indicate the presence or absence of these certain small molecules. For example, if the presence of a certain small molecule is essential for the efficacy of a particular therapeutic compound, then an assay can be developed to quickly determine the presence or absence of this certain small molecule in cell samples treated with test compounds. This can be both an effective and inexpensive method to determine the potential efficacy of compounds. It can be used alone or in combination with traditional drug screening assays such as, for example, binding assays and other enzymatic assays.

For example, in search of molecules with anti-tumor activity, small molecule profiles could be taken of cells at certain intervals after being treated with a known anti-tumor drug (e.g., taxol, cis platin, adriamycin, etc.). Comparison of the small molecule profiles of these cells could lead to the identification of small molecules regulated by these drug. The identified small molecules could then be used to guide drug discovery by pointing to pathways which could be targeted for drug design or by using them as therapeutic or nutriceutical agents. Furthermore, both the targets and the identified small molecules can be used in assays of the invention described in detail in later sections.

The invention also includes a method for determining the toxicity of a test compound, e.g., a compound in development as a therapeutic agent. The method includes culturing cells, contacting a portion of the cells with the test compound, taking small molecule profiles of both the cells contacted with the test compound, taking the small molecule profiles of cells not contacted with the test compound, and comparing the profiles to either each other or profiles from cells contacted with a known therapeutic agent or cells contacted with a known toxin. The method also can include a step of purifying a particular organelle of interest from the cells and obtaining the small molecule profile of the particular organelle of interest (e.g., nuclei, mitochondria, Golgi apparatus, endoplasmic reticulum, ribosome, etc.).

In a further embodiment, the invention pertains to a method for reducing side effects of drugs under development. For example, cells can be cultured, contacted with the test compound, the small molecule profile can be generated, and compared to the profiles of known toxins and therapeutic agents. Changes then can be made to the structure of the test compound to reduce the side effects. For example, in order to test for liver toxicity, the compound may be incubated the in a liver cell culture to mimic the biotransformation that occurs in the liver. The small molecule profiles of cells and organelles in the treated and untreated liver cultures can be compared to the small molecule profiles of known toxins. Both the total cellular small molecule profile could be compared or the small molecule profile of a particular organelle, e.g., mitochondria, Golgi apparatus, nuclei, ribosomes, endoplasmic reticulum, etc.

The methods of the invention are particularly useful because they offer a quick and relatively inexpensive method to determine whether a certain test compound is likely toxic to a body organ, such as the liver. This allows for pharmaceutical companies to quickly screen and identify compounds which are toxic and to direct their research towards non-toxic compounds.

The methods and small molecule profiles of the invention may also be used to rescue drugs, e.g., drugs which fail a particular step in the clinical or pre-clinical trial procedure. The failed drug can be exposed to cells or a test organism and small molecule profiles of the cells, cellular compartments, organelles, etc. can be taken and compared to those of known toxins, known therapeutic agents, etc. to pinpoint the reason for failure of the drug. Small molecule profiles of various organs can also be taken if it is advantageous for the study (e.g., small molecule profiles can be taken from muscle, brain, retinal, nerve, heart, lung, stomach, colon, skin, breast, fatty tissue, blood, etc.)Then the drug can be redesigned to avoid the its previous adverse effects.

The methods and small molecule profiles of the invention can also be used to "reposition" drugs.

The term "reposition" refers to discovering new uses for an agent. In one embodiment, a dose of an agent is administered to a subject (e.g., a human or other animal, healthy or diseased) and small molecule profiles are then taken from various organs, tissues, cells, cellular compartments, and/or organelles of the subject to determine what tissues, organs, cells, cellular compartments, and/or organelles are being affected by the administration of the agent.

4. Methods of Identifying Small Molecules Associated with Body Weight Disorders

The invention also pertains to methods for identifying small molecules associated with, for example, body weight disorders such as obesity. Examples of methods for identifying small molecules associated with body weight disorders are described below. The following experiment are directed to the identification of small molecules associated with short term appetite control. These experiments can be used to identify small molecules involved in signaling hunger and satiety.

In one embodiment, test subjects, preferably mice, will be fed normally prior to the initiation of the experiment, and then divided into one control and two experimental groups. The control group will then be maintained on ad lib nourishment, while the first experimental group ("fasted group") will be fasted, and the second experimental group ("fasted-refed group") will initially be fasted, and will then be offered a highly palatable meal shortly before the collection of tissue samples. Each test animal will be weighed immediately prior to and immediately after the experiment. Small molecule profiles will be taken of each mouse from each group. The profiles of each group will be averaged and compared to those of different groups. Example 2, below, demonstrates the use of such short term appetite experiments to identify small molecules which are present in different amounts in control versus fasting and versus refed animals.

Other experiments which may be used for the identification of cellular small molecules involved in, for example, body weight disorders, are experiments designed to analyze small molecules which may be involved genetic obesity. In the case of mice, for example, such experiments may identify small molecules regulated by the ob, db, and/or tub gene products. In the case of rats, for example, such paradigms may identify small molecules regulated by the fatty (fa) gene product.

In one embodiment of such an experiment, test subjects may include ob/ob, db/db, and/or tub/tub experimental mice and lean littermate control animals. The animals would be offered normal nourishment for a given period, after which tissue samples would be collected for analysis. Example 2, below, demonstrates the use of such genetic obesity paradigms in identifying small molecules which are present in different amounts in the small molecule profiles of obese versus lean animals.

In additional experiments, ob/ob, db/db, and/or tub/tub experimental mice and lean control animals may be used as part of the short term appetite control experiments discussed above, or in other experiments discussed herein, such as set-point experiments and drug related experiments.

Experiments which may be used for the identification of small molecules involved in body weight disorders may include experiments designed to identify those small molecules which may be regulated in response to changes in body weight, e.g., "set point experiments".

In one experiment, test subjects, preferably mice, will be fed normally prior to the initiation of the experiment, and then divided into one control and two experimental groups. The control group will then be maintained on an ad lib diet of normal nourishment in order to calculate daily food intake. The first experimental group ("underweight group") will then be underfed by receiving some fraction of normal food intake, 60–90% of normal, for example, so as to reduce and maintain the group's body weight to some percentage, for example 80%, of the control group. The second experimental group ("overweight group") will be overfed by receiving a diet which would bring the group to some level above that of the control, for example 125% of the control group. Tissue samples will then be obtained for analysis to identify small molecules which are present in different amounts in control versus overweight and/or underweight conditions.

Additionally, human subjects may be used for the identification of obesity-associated small molecules. In one embodiment of such an experiment, tissue samples may be obtained from obese and lean human subjects and analyzed for the presence of small molecules which are present in different amounts in the tissue, cells, or cellular organelles of one group as opposed to another (e.g. differentially present in lean versus obese subjects). In another embodiment, obese human subjects may be studied over the course of a period of weight loss, achieved through food restriction. Tissue from these previously obese subjects may be analyzed for differing amounts of small molecules relative to tissue obtained from control (lean, non-previously obese) and obese subjects.

Experiments may also be designed to identify of small molecules involved in body weight disorders and may also may include experiments designed to identify small molecules associated with body weight disorders induced by some physical manipulation to the test subject, such as, for example, hypothalamic lesion-induced body weight disorders. For example, bilateral lesions in the ventromedial hypothalamus (VMH) of rodents may be utilized to induce hyperphagia and gross obesity in test subjects, while bilateral lesions in the ventrolateral hypothalamus (VLH) of rodents may be used to induce aphagia in test subjects. In such experiments, tissue from hypothalamic-lesioned test subjects and from control subjects would be analyzed for the identification of small molecules which are present in different amounts in control versus lesioned animals.

Drugs known to affect (e.g., ameliorate) human or animal body weight and/or appetite (such as short term appetite) may be incorporated into the experiments designed to identify small molecules which are involved in body weight disorders and/or body weight or appetite regulation. These compounds may include known therapeutics, as well as compounds that are not useful as therapeutics due to, for example, their harmful side effects. Among the categories of control and test subjects which may be used in such experiments are, for example, lean subjects, obese subjects, and obese subjects which have received the drug of interest. In variations of the experiment, subjects such as these may be fed a normal ad lib diet, a caloric restriction maintained diet, or a caloric restriction ad lib diet. Control and test subjects may additionally be pairfed i.e., the control and test subjects may be fed via a coupled feeding device such that both control and test subjects receive identical amounts and types of food).

5. Methods of Identifying Small Molecules Associated with Immunological Diseases The invention also pertains to methods for identifying small molecules associated with, for example, normal and abnormal immune responses. Examples of methods for identifying small molecules associated with immune responses are described below. The following experiment are directed to the identification of small molecules which are differentially present within and among TH cell subpopulations, including but not limited to TH1 and TH2 subpopulations. Such small molecules can be involved in, for example, TH cell subpopulation differentiation, maintenance, and/or effector function, and in TH cell subpopulation-related disorders. For example, TH cells can be induced to differentiate into either TH1 or TH2 states, can be stimulated with, for example, a foreign antigen, and can be collected at various points during the procedure for analysis of their small molecule profiles. This example is merely meant to be illustrate several experiments which can be done using small molecule profiles to determine small molecules associated with immunological disorders. This example is not intended to limit the invention to the specific types of cells or subjects discussed in this section.

In one experiment, transgenic animals, preferably mice, will be used which have been engineered to express a particular T cell receptor, such that the predominant T cell population of the immune system of such a transgenic animal recognizes only one antigen. Such a system will be used because it provides a source for a large population of identical T cells whose naivete can be assured, and because its response to the single antigen it recognizes is also assured. T helper cells can be isolated from such a transgenic animal can then be induced, in vitro, to differentiate into TH cell subpopulations such as TH1, TH2, or TH0 cell subpopulations. In one embodiment, one T helper cell group (the TH1 group) is exposed to IL-12, a cytokine known to induce differentiation into the TH1 state, a second T helper cell group (the TH2 group) is exposed to IL-4, a cytokine known to induce differentiation into the TH2 state, and a third group is allowed, by a lack of cytokine-mediated induction, to enter a TH-undirected state. Small molecule profiles of each type of cells can then be taken and compared.

In another experiment, mature TH cell clones can be used, such as TH1 and TH2 and TH1-like and TH2-like cell lines, preferably human cell lines. Such TH cell lines can include, but are not limited to the following well known murine cell lines: Doris, AE7, D10.G4, DAX, D1.1 and CDC25. Such T cell lines can be derived from normal individuals as well as individuals exhibiting TH cell subpopulation-related disorders, such as, for example, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

The TH cell clones can be stimulated in a variety of ways. Such stimulation methods include, but are not limited to, pharmacological methods, such as exposure to phorbol esters, calcium ionophores, or lectins (e.g., Concanavalin A), by treatment with antibodies directed against T-cell receptor epitopes (e.g., anti-CD3 antibodies) or exposure, in the presence of an appropriate antigen presenting cell (APC), to an antigen that the particular TH cells are known to recognize. Following such primary stimulation, the cells can be maintained in culture without stimulation and, for example, in the presence of IL-2, utilizing standard techniques well known to those of skill in the art. The cells can then be exposed to one or more additional cycles of stimulation and maintenance. The small molecule profiles of the cells o cellular compartments can be taken at any time during the process of the stimulation in this experiment.

A third experiment can also be used to discover determine small molecules present in different amounts. In vivo stimulation of animal models forms the basis for this experiment. The in vivo nature of the stimulation can prove to be especially predictive of the analogous responses in living patients. Stimulation can be accomplished via a variety of methods. For example, animals, such as transgenic animals described earlier, can be injected with appropriate antigen and appropriate cytokine to drive the desired TH cell differentiation. Draining lymph nodes can then be harvested at various time points after stimulation. Lymph nodes from, for example, TH1-directed animals can be compared to those of TH2-directed animals. A wide range of animal models, representing both models of normal immune differentiation and function as well as those representing immune disorders can be utilized for this in vivo experiment.

Cell or organelle samples can be collected during any point of such a procedure for small molecule profiling. For example, cells or organelles can be obtained following any stimulation period and/or any maintenance period. Additionally, the cells or organelles can be collected during various points during the TH cell differentiation process. The small molecule profiles of the cells or organelles can be compared using the methods outlined in the Examples. For example, small molecule profiles from TH0, TH1 and TH2 groups isolated at a given time point can then be analyzed and compared. Additionally, small molecule profiles from stimulated and non-stimulated cells within a given TH cell group can also be compared and analyzed. Further, small molecule profiles from undifferentiated TH cells can be compared to small molecule profiles from cells at various stages during the differentiative process which ultimately yields TH cell subpopulations.

6. Methods of Identifying Small Molecules Associated with Cardiovascular Disorders The small molecule profiles of the invention can be used to identify small molecules which are relevant to cardiovascular disease.

According to the invention, profiles are generated for small molecules present in endothelial cells or endolethial cell organelles subject to fluid shear stress in vitro. Shear stress may be responsible for the prevalence of atherosclerotic lesions in areas of unusual circulatory flow.

Cell cultures are exposed to fluid shear stress which is thought to be responsible for the prevalence of atherosclerotic lesions in areas of unusual circulatory flow. Unusual blood flow also plays a role in the harmful effects of ischemia/reperfusion, wherein an organ receiving inadequate blood supply is suddenly reperfused with an overabundance of blood when the obstruction is overcome.

Cultured HUVEC monolayers are exposed to laminar shear stress by rotating the culture in a specialized apparatus containing liquid culture medium (Nagel et al., 1994, *J. Clin. Invest.* 94: 885–891). Static cultures grown in the same medium serve as controls. After a certain period of exposure to shear stress, experimental and control cells will be harvested, organelles isolated and small molecule profiles will be generated to identify molecules which are present in exposed versus control cells.

In experiments designed to identify small molecules which are involved in cardiovascular disease, compounds such as drugs known to have an ameliorative effect on the disease symptoms may be incorporated into the experimental system. Such compounds may include known therapeutics, as well as compounds that are not useful as therapeutics due to their harmful side effects. Test cells that are cultured, for example, may be exposed to one of these compounds and analyzed for different small molecule profiles with respect to untreated cells, according to the methods described below in the Examples. In principle, according to the particular experiment, any cell type involved in the disease may be treated at any stage of the disease process by these therapeutic compounds.

Test cells may also be compared to unrelated cells (e.g., fibroblasts) that are also treated with the compound, in order to screen out generic effects on small molecule profiles that may not be related to the disease. Such generic effects might be manifest by changes in small molecule profiles that are common to the test cells and the unrelated cells upon treatment with the compound.

By these methods, the small molecules upon which these compounds affect can be identified and used in the assays described below to identify novel therapeutic compounds for the treatment of cardiovascular disease.

In another experiment, small molecules are identified from monocytes from human subjects. This experiment involves differential treatment of human subjects through the dietary control of lipid consumption. The human subjects are held on a low fat/low cholesterol diet for three weeks, at which time blood is drawn, monocytes are isolated according to the methods routinely practiced in the art, organelles, such as mitochondria, nuclei, and the cytosol, are isolated and profiles are generated. These same patients are subsequently switched to a high fat/high cholesterol diet and monocyte organelles are purified again. The patients may also be fed a third, combination diet containing high fat/low cholesterol and monocyte organelles may be purified once again. The order in which patients receive the diets may be varied. The small molecules of the organelles derived from patients maintained on two of the diets, or on all three diets, may then be compared and analyzed.

In addition to the detection of different small molecule profiles in monocytes, paradigms focusing on endothelial cells may be used to detect small molecules involved in cardiovascular disease. In one experiment, human umbilical vein endothelial cells (HUVEC's) are grown in vitro. Experimental cultures will then be treated with human IL-1β, a factor known to be involved in the inflammatory response, in order to mimic the physiologic conditions involved in the atherosclerotic state. Alternatively experimental HUVEC cultures may be treated with lysophosphatidylcholine, a major phospholipid component of atherogenic lipoproteins or oxidized human LDL. Control cultures are grown in the absence of these compounds. After a certain period of treatment, experimental and control cells will be harvested and small molecule profiles will be taken of the cells and/or organelles and analyzed.

7. Methods of Identifying of Small Molecules Associated with Central Nervous System and other Neurological and Neurodegenerative Disorders The small molecule profiles of the invention can be used to identify small molecules which are relevant to central nervous system and other neurological and neurodegenerative disorders. Examples of such disorders include, for example, neuropathies, Alzheimer disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, aging, dementia, peripheral nervous system diseases and mental disorders such as depression and schizophrenia, etc.

One method for identifying small molecules which are relevant to central nervous system and other neurological and neurodegenerative disorders, is to compare the small molecule profiles of a diseased cell, cellular compartment or organelle of a diseased organism to a small molecule profile of a healthy cell, cellular compartment, or organelle (e.g., a standard small molecule profile) For example, the cells can be derived from the subjects' brain, muscle, retinal, nerve tissue, spinal fluid, blood, etc.

The diseased organism can be either a human or animal patient suffering from a neurological disorder or from an animal model of such a disorder. In certain embodiments, the invention pertains to the small molecules which are found in aberrant amounts in the small molecule profiles of diseased cells. In other embodiments, the invention pertains to the small molecule subtraction profiles of particular neurological disorders (e.g., subtraction profiles of the diseased small molecule profile compared to the standard small molecule profile, etc.).

8. Methods of Identifying Small Molecules Associated with Oncological Disorders In one embodiment, the invention pertains to methods of identifying small molecules associated with oncological disorders, e.g., cancerous tumors, leukemia, lymphoma, etc.

In one embodiment, small molecules associated with an oncological disorder are identified by comparing small molecule profiles of cancerous tissue with normal tissue. In a further embodiment, the tissue is from the same individual, e.g., normal and malignant prostate tissues are excised from a mammalian subject, e.g., mouse, rat, or human. Small molecule profiles of cells, cellular compartments, or organelles of the normal tissue is compared with the corresponding small molecule profiles of the malignant tissue. When the small molecule profiles are compared, certain small molecules may appear to be present in aberrant amounts in the cancerous tissue.

The invention also pertains to methods for detecting aberrant amounts of the identified compound in other tissue, e.g., the methods of the invention can be used to develop a reagent that specifically reacts with cancerous tissue.

9. Methods of Identifying Small Molecules Regulated by Genes of Interest

In another embodiment, the invention pertains to methods of identifying small molecules regulated, modulated, or associated with genetic modification or alterations of cells, both engineered and naturally occurring. The identified small molecules can be used, for example, to determine the function of unknown genes in functional genomics. For example, the comparison of the small molecules found in genetically altered cells can be used to elucidate the function of any given gene. For example, the invention pertains to a method for identifying small molecules associated with expression vectors of interest by comparing the small molecules of host cells expressing an expression vector to the small molecules of host cells not expressing the expression vector. In one embodiment, the expression vector comprises a portion or fragment of the genome, e.g., human genome. In another embodiment, the expression vector may be known to be associated with a particular disease state. The small molecules of the cells with and with out the expression vector expressed can be used to identify small molecules of interest, pathways of interest, and targets for drug design and/or future study.

In a further embodiment, the small molecules of the cells are identified by through separation techniques such as HPLC, mass spectroscopy and coulometric array technology to create small molecule profiles (see, for example, Kristal, B. S. et al. *Anal. Biochem.* 263:18–25 (1998)). The resulting small molecule profile can then be compared to the small molecule profile of other cells, e.g., cells not genetically modified.

The term "vector" includes nucleic acid molecules capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The recombinant expression vectors of the invention can be designed for expression in prokaryotic or, preferably, eukaryotic host cells. For example, the vectors can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990).

Expression of vectors in prokaryotes is most often carried out in *E. coli* with vectors containing constitutive or inducible promoters directing the expression of either fusion or non-fusion proteins. Examples of inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

In another embodiment, the expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, the vector can be expressed in insect cells using baculovirus expression vectors. Baculovirus vectors available for expression of vectors in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In a preferred embodiment, a nucleic acid of the interest is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The terms "host cell" and "recombinant host cell" are used interchangeably. These cells include not only the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

For this method, a host cell can be any prokaryotic or eukaryotic cell. For example, a protein of interest can be expressed in bacterial cells such as *E. coli*, insect cells, yeast or, preferably, mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. The terms "transformation" and "transfection" include a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as the gene or a separate vector. Cells stably transfected with the introduced nucleic acid can be identified by drug selection (e.g., cells that have incorporated the selectable marker gene will survive, while the other cells die).

Furthermore, in yet another embodiment, the invention also pertains to methods for identifying small molecules regulated by a gene expressed in a particular host cell. In this embodiment, the gene is removed, functionally disrupted, otherwise not expressed in the cell and the small molecules of the cell are compared to those of a similar cell wherein the gene is expressed. The small molecules which are regulated, modulated or associated with this gene can then be identified by the comparison of the small molecules of the cells with and without the gene expressed. The small molecules which are present in aberrant amounts can then be used to identify pathways, targets, and other small molecules associated with this gene, using methods of the invention.

To functionally disrupt a gene of a cell, a vector is prepared which contains at least a portion of a gene of interest into which a deletion, addition or substitution has been introduced to thereby alter, e.g., functionally disrupt, the gene of interest. The gene of interest can be a human gene, or a non-human homologue of a human gene. In an embodiment, the vector is designed such that, upon homologous recombination, the endogenous gene of interest is functionally disrupted (i.e., no longer encodes a functional protein; also referred to as a "knock out" vector). Alternatively, the vector can be designed such that, upon homologous recombination, the endogenous gene of interest is mutated or otherwise altered but still encodes, for example, a functional protein (e.g., the upstream regulatory region can be altered to thereby alter the expression of the endogenous protein). In the homologous recombination vector, the altered portion of the gene of interest is flanked at its 5' and 3' ends by additional nucleic acid sequence of the gene of interest to allow for homologous recombination to occur between the exogenous gene of interest carried by the vector and an endogenous gene of interest in a cell. The additional flanking nucleic acid sequence should be of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into a cell line (e.g., by electroporation) and cells in which the introduced gene of interest has homologously recombined with the endogenous gene of interest are selected (see e.g., Li, E. et al. (1992) *Cell* 69:915). The small molecules of the cells can then be compared to cells with out the gene of interest disrupted, thus identifying small molecules associated with the gene of interest.

10. Assays for Identifying Potential Cell Drug Targets Using Labeled Disease Relevant Small Molecules In another embodiment, the invention also pertains to methods for identifying potential cell drug targets (e.g., cellular components which interact with the labeled small molecules). This method is particularly useful because it can identify components which are known to interact with disease relevant small molecules. Therefore, targets identified through this method are "pre-validated," and some of the guess work surrounding the choice of target is eliminated. In a further embodiment, this method can be used in conjunction with conventional genomics as a further validation step to identify targets for further research.

The method includes obtaining a cell from a source, obtaining samples of small molecules from the cell; testing the samples for biological activity; identifying the biologically active small molecules of the samples; labeling the biologically active small molecules; contacting the labeled small molecules with cellular components; and identifying interactions between cellular components and said labeled small molecules. The invention includes the identified cell drug targets as well as the identified biologically active small molecules.

In another embodiment, the invention includes a method for identifying potential cell drug targets. The method includes contacting a labeled disease relevant small molecule with cellular components; and identifying interactions between said cell components and the labeled disease-relevant small molecule.

The labeled small molecules also include labeled "disease-relevant small molecules," identified by any of the techniques described herein (e.g., comparison of small molecule profiles in healthy and diseased cells, etc.). In another embodiment, the method includes contacting a labeled disease relevant small molecule with cellular components, and identifying the interactions between the cellular components and the labeled disease relevant small molecule.

The term "label" includes any moieties or molecules which enhance the ability of the labeled small molecules to be detected. Examples of suitable labels are well known in the art. radiolabels and fluorescent labels. The term "label" includes direct labeling of the small molecule by radiolabeling, coupling (i.e., physically linking) a detectable substance (e.g., a fluorescent moiety) to the small molecule, and indirect labeling of the small molecule by reacting the small molecule with another reagent that is directly labeled. Examples of indirect labeling include detection of a small molecules by labeling it with biotin such that it can be detected with fluorescently labeled streptavidin. In one embodiment, the small molecules are fluorescently labeled or radiolabeled.

The term "cellular components" includes material derived from cells. The cellular components can be purified or crude cellular extracts. The cellular components can be derived from one type of cell, or even a specific cellular compartment such as an organelle (e.g., mitochondria, nucleus, cytoplasm). Furthermore, the term includes both natural proteins found within biological systems and chimeric and other engineered proteins. In one embodiment, the term "cellular component" includes cellular receptors. The term also includes natural and unnatural polysaccharides and nucleic acids. In one embodiment, the term "cellular component" is a crude cellular extract from a human cell. The term "cellular component" includes "targets."

Samples of the invention that bind to cellular components can be identified by preparing a reaction mixture of the cellular components and the samples under conditions and for a time sufficient to allow the components and the sample to interact and bind, thus forming a complex which can be removed and/or detected in the reaction mixture. The cellular components used can vary depending upon the goal of the screening assay. In one embodiment, the sample of the invention is an isolated, labeled small molecule, e.g., a disease relevant small molecule, a small molecule with biological activity or another small molecules which is present in aberrant levels in disease states. The assay can be used to determine which cellular components the small molecule interacts with. The identified cellular components which interact with the small molecule can then be used for drug design.

In a further embodiment, the cellular components are a nucleic acid array. High density arrays of nucleic acids (such as cDNA's and synthetic oligonucleotides) allow for a high degree of automation, repetitive analysis and duplication at minimal cost (Fraser, *Electrophoresis*, 18:1207–1215 (1997)). The development of recent technology has provided methods for making very large arrays of oligonucleotide probes in very small areas (see, for example, U.S. Pat. No. 5,143,854, WO 90/15070 and WO 92/10092, each of which is incorporated herein by reference). In one embodiment, the nucleic acids of the array are human genes. Examples of nucleic acid arrays include those mentioned in U.S. Pat. Nos. 6,027,880 and 5,861,242. The nucleic acids also can be representative of RNA molecules present in a cell, tissue or organ (e.g., the "transcriptome", see Hoheisel, J. et al. *Trends Biotechnol.* 15:465–469 (1997); Velculescu, *Cell*, 88:243–251 (1997)). In one embodiment, the nucleic acids are in array.

In another further embodiment, the cellular components are a protein array. Examples of protein arrays include those employing conventional protein separation techniques, such as 2-dimensional gel electrophoresis, chromatographic procedures (e.g., FPLC, SMART by Pharmacia, Uppsala, Sweden), capillary electrophoretic techniques and mass spectrometry. In another embodiment, the protein array is a soup of proteins that contains a significant portion of the diversity encoded by a genome (see WO 99/39210).

In a further embodiment, the cellular components are a 2D protein gel. The 2D protein gel may be a complete or an incomplete set of the protein molecules present in a cell, tissue or organ (e.g., the proteome, see Sagliocco, et al. *Yeast* 12, 1519–1534 (1996); Shevalanko, et al. *Porch. Nat. Acad. Sci.* 93, 14440–14445 (1996)). Labeled biologically active small molecules previously identified through methods of the invention can then be contacted with the 2D gels and interactions between the labeled small molecules and the protein of the 2D gel can be detected.

The proteins identified through this method can then be further tested for biological activity, e.g., biological activity relating to that of the small molecule, e.g., through knock-out mice, inhibition studies, and other techniques known in the art. Furthermore, the identified proteins can then be used in drug design to identify other molecules (either naturally occurring or chemically synthesized) which bind or interact with the protein which may have advantageous characteristics (e.g., enhanced biological activity, less toxic side effects).

11. Predictive Medicine and Pharmacometabolomics

The present invention also pertains to the field of predictive medicine in which diagnostic assays, prognostic assays, pharmacometabolomics, and monitoring clinical trails are used for prognostic (predictive) purposes to thereby treat an individual prophylactically. Accordingly, one aspect of the present invention relates to diagnostic assays for determining small molecule profiles, in the context of a biological sample (e.g., blood, serum, cells, tissue, cellular organelles) to thereby determine whether an individual is afflicted with a disease or disorder, or is at risk of developing a disorder, associated with aberrant levels of small molecules. The invention also provides for prognostic (or predictive) assays for determining whether an individual is at risk of developing a disorder associated with relevant small molecules. For example, aberrant levels of small molecules can be profiled from a biological sample. Such assays can be used for prognostic or predictive purpose to thereby prophylactically treat an individual prior to the onset of a disorder characterized by or associated with a relevant small molecule.

Another aspect of the invention provides methods for determining small molecule profiles of an individual to thereby select appropriate therapeutic or prophylactic agents for that individual (referred to herein as "pharmacometabolomics"). Pharmacometabolomics allows for the selection of agents (e.g., drugs) for therapeutic or prophylactic treatment of an individual based on the small molecule profile of the individual (i.e., the individual's "metaboprint"). The metaboprint of the individual is examined to predict what the person's reaction to a particular therapeutic compound will be. Yet another aspect of the invention pertains to monitoring the influence of agents (e.g., drugs or other compounds) on the small molecule profiles of the patients in clinical trials.

Pharmacometabolomics is similar to pharmacogenomics but it is also able to taken in to account environmental and other non-genetic factors (e.g., other drugs, etc.) which may affect an individual's response to a particular therapeutic compound. Pharmacometabolomics can be used alone or in combination with pharmacogenomics to predict an individual's reaction to a particular drug based upon their metaboprint (e.g., small molecule profile) and/or their genotype.

Pharmacometabolomics is particularly useful because it provides an early warning sign, due to its capability of detecting aberrant small molecules long before any disease symptoms or predisposed phenotypes are noticed.

A. Diagnostic Assays

In one embodiment, the invention pertains to a method for facilitating the diagnosis of a disease state of a subject. The method includes obtaining a small molecule profile from a subject suspected of having and/or having a disease state, and comparing the small molecule profile from the subject to a standard small molecule profile.

The invention provides a method of assessing small molecule profiles, especially aberrant small molecule profiles. Aberrant small molecule profiles (e.g., excessive amounts of a particular molecule, deficient amounts of a particular molecule, the presence of a small molecule not usually present, etc.) may indicate the presence of a disease state. More generally, aberrant small molecule profiles may indicate the occurrence of a deleterious or disease-associated metaboprint contributed by small molecules present in aberrant amounts.

The standard small molecule profile can be obtained from healthy subjects or subjects afflicted with the disease state which is the subject is suspected of having. The small molecule profiles can be taken from a particular organ, tissue, or combinations or organs or tissues. The small molecule profiles can also be taken of cells, cellular compartments, or particular organelles.

The term "disease state" includes any states which are capable of being detected metabolomically by comparing small molecule profiles of a subject having the disease to a standard small molecule profile. Examples of disease states include, but are not limited to, include metabolic diseases (e.g., obesity, cachexia, diabetes, anorexia, etc.), cardiovascular diseases (e.g., atherosclerosis, ischemia/reperfusion, hypertension, restenosis, arterial inflammation, etc.), immunological disorders (e.g., chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy, etc.), nervous system disorders (e.g., neuropathies, Alzheimer disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, bacterial infection, fungal infection, stroke, aging, dementia, peripheral nervous system diseases and mental disorders such as depression and schizophrenia, etc.), oncological disorders (e.g., leukemia, brain cancer, pancreatic cancer, prostate cancer, liver cancer, stomach cancer, colon cancer, throat cancer, breast cancer, ovarian cancer, skin cancer, melanoma, etc.). The term also include disorders which result from oxidative stress.

The term "subject" includes humans, animals, and plants. In one embodiment, the subject is a human suffering from or at risk of suffering from a disease state.

The invention also encompasses kits for detecting the presence of a particular relevant small molecule in a biological sample (a test sample). Such kits can be used to determine if a subject is suffering from or is at increased risk of developing a disorder associated with the relevant small molecule (e.g., drug resistance). For example, the kit can comprise a labeled compound or agent capable of detecting the relevant small molecule in a biological sample and means for determining the amount of the relevant small molecule in the sample (e.g., an antibody against the relevant small molecule another molecular or chemical sensor). Kits may also include instruction for observing that the tested subject is suffering from or is at risk of developing a disorder associated with the relevant small molecule if the amount of the relevant small molecule is above or below a normal level.

The kit may also comprise, e.g., a buffering agent, a preservative, or a stabilizing agent. The kit may also comprise components necessary for detecting the detectable agent (e.g., a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with the relevant small molecule.

B. Prognostic Assays

The invention also pertains to a method for predicting whether a subject is prediposed to having a disease state. The method includes obtaining a small molecule profile from the subject; and comparing the small molecule profile from the subject to a standard small molecule profile, thereby predicting whether a subject is prediposed to having a disease state.

The methods described herein can furthermore be used as diagnostic or prognostic assays to identify subjects having or at risk of developing a disease or disorder associated with aberrant small molecule profiles. For example, the assays described herein, such as the preceding diagnostic assays or the following assays, can be utilized to identify a subject having or at risk of developing a disorder associated with an aberrant small molecule profile, such as drug resistance of tumor cells. Alternatively, the prognostic assays can be utilized to identify a subject having or at risk for developing such a disease or disorder. Thus, the present invention provides a method in which a test sample is obtained from a subject and a small molecule profile is taken, wherein an aberrant small molecule profile is diagnostic for a subject having or at risk of developing a disease or disorder associated with an aberrant small molecule profile. The term "test sample" is a biological sample obtained from a subject of interest. For example, a test sample can be a biological fluid (e.g., serum), cell sample, or tissue. Advantageously, the test sample may consist of cells or individual organelles, e.g., mitochondria, nuclei, Golgi apparatus, endoplasmic reticulum, ribosomes, chloroplasts, etc.

Furthermore, the prognostic assays described herein can be used to determine whether a subject can be administered an agent (e.g., peptidomimetic, protein, peptide, nucleic acid, small molecule, or other drug candidate) to treat a disease or disorder associated with an aberrant small molecule profile. For example, such methods can be used to determine whether a subject can be effectively treated with a specific agent or class of agents (e.g., agents of a type which effect the small molecule profile in particular ways). Thus, the present invention provides methods for determining whether a subject can be effectively treated with an agent for a disorder associated with an aberrant small molecule profile in which a test sample is obtained and an aberrant small molecule profile is detected (e.g., wherein the presence or relative quantity of particular relevant small molecules is diagnostic for a subject that can be administered the agent to treat a disorder associated with the aberrant small molecule profile). In some embodiments, the foregoing methods provide information useful in prognostication, staging and management of particular states that are characterized by altered small molecule profiles and thus by a particular metaboprint. The information more specifically assists the clinician in designing treatment regimes to eradicate such particular states from the body of an afflicted subject.

The methods of the invention can also be used to detect the presence or absence of relevant small molecules, thereby determining if a subject is at risk for a disorder associated with this relevant small molecule. For example, the presence or absence of relevant small molecules, may indicate whether the process of developing a disease state has been initiated or is likely to arise in the tested cells. In preferred embodiments, the methods include detecting the presence or absence of the relevant small molecule, in a sample of cells from the subject, the presence or absence of a disease state. Preferably the sample of cells is obtained from a body tissue suspected of comprising diseased cells. Thus, the present method provides information relevant to diagnosis of the presence of a disease state. In one embodiment, the sample of cells is comprised mainly of a particular cellular organelle, e.g., mitochondria, Golgi apparatus, nuclei, etc.

The methods described herein may be performed, for example, by utilizing pre-packaged diagnostic kits comprising at least one reagent for detecting a relevant small molecule, which may be conveniently used, e.g., in clinical settings to diagnose patients exhibiting symptoms or family history of a disease or illness involving a relevant small molecule.

C. Pharmacometabolomics

The invention also pertains to a method for predicting a subject's response to a therapeutic agent. The method includes obtaining a small molecule profile from the subject, and comparing the small molecule profile of the subject to a known standard established for the therapeutic agent as an indication of whether the subject would benefit from treatment with the therapeutic agent.

Agents, or modulators which alter levels of particular relevant small molecules, as identified by a screening assay described herein can be administered to individuals to treat (prophylactically or therapeutically) disorders associated with the relevant small molecules. In conjunction with such treatment, the pharmacometabolomics (i.e., the study of the relationship between an individual's metaboprint and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacometabolomics of the individual permits the selection of effective agents (e.g., drugs) for prophylactic or therapeutic treatments based on a consideration of the individual's metaboprint. Such pharmacometabolomics can further be used to determine appropriate dosages and therapeutic regimens. Accordingly, the small molecule profile of an individual can be determined to thereby select appropriate agent(s) for therapeutic or prophylactic treatment of the individual.

The known standard can be obtained from subjects who benefited from the agent, e.g., patients who were treated with the agent and were cured, maintained their health, or prevented or slowed the deterioration of health. The known standard can be taken from a particular tissue, organ. It can also be taken from any organelle, cell, or cellular compartment during any point during the beneficial treatment. It can be derived from a single patient or from an average of more than one patient who were treated successfully with the agent. In addition, the known standard can also be derived using other techniques.

Pharmacometabolomics deals with clinically significant hereditary and non-hereditary variations in the response to drugs due to altered drug disposition and abnormal action in affected persons. In general, several types of pharmacometabolomic conditions can be differentiated. For example, certain pharmacometabolomic conditions may be the result of genetic conditions. The genetic conditions may be transmitted as a single factor altering the way drugs act on the body (altered drug action) or genetic conditions transmitted as single factors altering the way the body acts on drugs (altered drug metabolism). These pharmacometabolomic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans. Examples of non-hereditary conditions which may affect the way drugs act on the body or the way the body acts on the drugs include the ingestion of certain drugs, the substance dependence of the patient, the diet of the patient, non-hereditary medical conditions of the patient, etc.

The small molecule profile and metaboprint an individual can be determined to select appropriate agent(s) for therapeutic or prophylactic treatment of the individual. In addition, pharmacometabolomic studies can be used to identify an individual's drug responsiveness metaboprint. This knowledge, when applied to dosing or drug selection, can avoid adverse reactions or therapeutic failure and thus enhance therapeutic or prophylactic efficiency when treating a subject with an agent, such as an agent identified by one of the exemplary screening assays known in the art.

D. Monitoring of Effects During Clinical Trials

The invention also pertains to a method for metabolomically monitoring the effectiveness of a therapeutic agent in clinical trials. The method includes obtaining a small molecule profile from a subject in a clinical trial being treated with a therapeutic agent, and monitoring changes in the small molecule profile of the subject as an indication of the effectiveness of the therapeutic agent in the subject. In one embodiment, the small molecule profile of the subject can be compared to a predetermined standard.

Monitoring the influence of agents (e.g., drugs, therapeutic compounds) on the small molecule profile can be applied not only in basic drug screening, but also in clinical trials. For example, the effectiveness of an agent determined by a screening assay as described herein to increase levels of certain relevant small molecules, can be monitored in clinical trails of subjects exhibiting decreased levels of certain small molecules. Alternatively, the effectiveness of an agent determined by a screening assay to decrease levels of a certain relevant small molecule, can be monitored in clinical trails of subjects exhibiting increased levels of the certain relevant small molecule. In such clinical trials, the level of the certain small molecule and, preferably, the remainder of the small molecule profile can be used as a "read out" of the disease state of the particular cell.

For example, and not by way of limitation, small molecules that are modulated in cells by treatment with an agent (e.g., compound, drug or small molecule) can be identified in screening assays. The effect of agents on cellular proliferation disorders, for example, can be studied in a clinical trial. For example, cells can be isolated and small molecule profiles of either whole cells or particular organelles can be taken. In this way, the small molecule profile can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the small molecule profile of the preadministration sample; (iii) obtaining one or more post-administration samples from the subject; (iv) detecting the small molecule profile of the post-administration samples; (v) comparing the small molecule profile of the pre-administration sample with the small molecule profile of the post administration sample or samples; and (vi) altering the administration of the agent to the subject accordingly. For example, increased administration of the agent may be desirable to increase the level of certain relevant small molecules to higher levels than detected, i.e., to increase the effectiveness of the agent. Alternatively, decreased administration of the agent may be desirable to decrease the level of certain relevant small molecules to lower levels than detected, i.e., to decrease the effectiveness of the agent.

12. Identification of Compounds which Protect Mitochondrial Function

In a further embodiment, the samples are obtained from a specific organelle, e g., mitochondria, nuclei, ribosomes, Golgi apparatus, endoplasmic reticulum, etc. The small molecule profiles obtained from the organelles can be used to identify small molecules which are of particular relevance to the particular organelle, in both health and disease states. In one embodiment, the invention pertains to standard small molecule profiles of particular organelles, e.g., nuclei, mitochondria, chloroplasts, Golgi apparatus, endoplasmic reticulum, ribosomes, etc.

The term "standard small molecule profiles of particular organelles" includes the averaged profiles of particular organelles. The standard profiles can be averaged over more than one profile from a particular individual, or from a population. Furthermore, the profiles can all be from the same type of cells (e.g., liver cells, muscle cells, nerve cells, brain tissue cells, blood cells, immune system cells, etc.) or different types of cells. The standard profiles can be taken of any organelle of interest. The organelle of interest can be obtained, generally, through methods known in the art, such as fractional centrifugation. Examples of organelles which can be analyzed through this method include, for example, nuclei, mitochondria, chloroplasts, centrioles, ribosomes, Golgi apparatus, endoplasmic reticulum, etc.

In one embodiment, the organelles are mitochondria. Mitochondrial dysfunction has been implicated in a wide range of physiological conditions, such as neurodegenerative diseases, aging processes, diabetes, and cancer. Mitochondria buffer intracellular calcium, are responsible for production of ATP, and play a key role in cell death pathways, such as apoptosis (Green and Reed, *Science* 281: 1309–1312, 1998; Susin et al., *Biochim. Et. Biophys. Acta* 1366: 151–165, 1998). Due to their central role in a wide array of cellular respiratory, oxidative and metabolic processes, defects in mitochondrial activity impact the rate of ATP production, calcium homeostasis, free radical production and release of apoptosis inducing factors. (Emster and Schatz, *J. Cell Biol.* 91:227s–255, 1981).

Therefore, in one embodiment, the invention pertains to a method for identifying compounds relevant to mitochondrial related disorders. In one embodiment, the invention pertains to small molecule profiles of mitochondria which identify about 70% or more of the small molecules, about 75% or more of the small molecules, about 80% or more of the small molecules, about 85% or more of the small molecules, about 90% or more of the small molecules, about 91% or more of the small molecules, about 92% or more of the small molecules, about 93% or more of the small molecules, about 94% or more of the small molecules, about 95% or more of the small molecules, about 96% or more of the small molecules, about 98% or more of the small molecules, about 99% or more of the small molecules of the mitochondria. In another embodiment, the invention pertains to methods for identifying compounds which are present in aberrant amounts when standard small molecule profiles of mitochondria are compared to small molecule profiles of mitochondria afflicted with a mitochondrial related disorder. The invention pertains to both the standard mitochondria profile and the compounds identified to be relevant to mitochondria related disorders.

The term "mitochondrial related disorders" include disorders associated with processes associated with the mitochondria. Mitochondrial related disorders include neurodegenerative diseases, aging, diabetes, and cancer. Further more mitochondrial related diseases included those related to the production of ATP, intracellular calcium, free radicals, and apopotosis.

In another embodiment, the compounds identified from the small molecule profile of the mitochondria are assayed for biologically active small molecules which protect mitochondrial function. Examples of assays that can be used for evaluating mitochondrial function include assays which evaluate the inhibition of production of reactive oxygen species (e.g., assays using dichlorofluorescin diacetate), assays for mitochondrial permeability transition (MPT) (e.g., assays using dyes such as 2–4dimethylaminostyryl-N-Methlypyridinim); mitochodrial electrochemical potential gradients; and cell death assays with signals which can be used to induce insult, measure or release apoptogenic molecules, structural changes in cells, DNA changes, activation of caspases, and translocation of membrane components. Assays that evaluate effects of compounds on electron transport chain are also included (Parker et al., *Neurology* 44: 1090–96, 1994; Miller et al., *J. Neurochem.* 67: 1897, 1996). In another embodiment, the compounds which are determined to be present in aberrant amounts in mitochondrial related disorders are assayed for protecting function. The invention also pertains to a pharmaceutical composition comprising any compound identified by the assays described herein and a pharmaceutically acceptable carrier.

In a further embodiment, the biologically active small molecules are chemically modified to enhance their biological activity. It is known in the art that through chemical modifications, one can enhance the biological activity, stability, or otherwise modify a molecule to make it more suitable as a therapeutic or nutriceutical agent.

13. Small Molecules Libraries and Methods of Use

In one embodiment, the invention pertains to the creation of small molecule libraries from cells, cellular compartments, and organelles, e.g., cells, cellular compartments, and organelles in health, diseased, and altered states. The small molecule libraries can be derived from the same or different animal organs. For example, the small molecule libraries can be derived from cells of the heart, brain, kidney, liver, done, blood, gastrointestinal tract, and/or muscle. In addition, the small molecule libraries can be derived from individuals suffering from a particular disease state, e.g., cardiovascular diseases, neurodegenerative diseases, diabetes, obesity, immunological disorders, etc.

The creation of the libraries involves fractionating cell components, preparing cellular extracts, and fractionating the small molecules by methods such as HPLC, thin layer chromatography (TLC), electrochemical techniques and other methods known in the art for separating such compounds. The compounds can be also separated using their charge, mass, hydrophilicity, and hydrophobicity. Furthermore, the compounds can be characterized using methods such as Mass Spectroscopy, NMR, IR, and other techniques known in the art for identifying organic compounds.

The term "library" includes searchable populations of small molecules or mixtures of molecules. In one embodiment, the library is comprised of samples or test fractions (either mixtures of small molecules or isolated small molecules) which are capable of being screened for activity. For example, the samples could be added to wells in a manner suitable for high throughput screening assays. In a further embodiment, the library could be screened for binding compounds by contacting the library with a target of interest, e.g., a protein or a nucleic acid.

In further embodiment, the invention pertains to a library of compounds from cells on a solid support, e.g., a solid support suitable for screening assays, e.g., a solid support suitable for high throughput assays. The invention also pertains to a cellular small molecule library packaged in a container comprising the small molecule library, a solid support, and a label identifying the contents.

In yet another embodiment, the small molecule libraries are derived from specific cellular compartments, e.g., the cytoplasm, the nucleus, the mitochondria, the choloroplast.

In one embodiment, the samples are screened for activity as a library. Within the last decade, small molecule libraries have been generated using combinatorial chemistry techniques to identify biologically active molecules. For example, libraries of compounds have been screened for biological activity using high throughput assays. For example, anti-tumor assays involve adding compounds to cancer cells in plastic wells and monitoring the effects of the compounds on cell survival. The compounds which effect cell survival, are identified as potential lead molecules.

Libraries can be screened to determine whether any samples of the library have a desired activity, and, if so, to identify the active compound or sample. Methods of screening libraries have been described (see, e.g., Gordon et al., *J Med. Chem.*). Soluble small molecule libraries can be screened by affinity chromatography with an appropriate receptor to isolate ligands for the receptor, followed by identification of the isolated ligands by conventional techniques (e.g., mass spectrometry, NMR, and the like). Immobilized samples can be screened by contacting the samples with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized samples can be selectively released and allowed to diffuse through a membrane to interact with a receptor.

In vitro systems may be designed to identify the samples of the libraries of the invention capable of interacting with targets of interest. The identified samples may contain useful compounds which may, for example, modulate the activity of the target; be useful in elaborating the biological function of the target; be utilized in screens for identifying additional compounds that disrupt the normal interactions of the target; or be useful themselves as disrupters of such interactions.

The term "target" includes proteins and mixtures of proteins (e.g., naturally occurring proteins, polypeptides, peptidomimitics, mutant proteins, and recombinant proteins). The term "target" also includes nucleic acid and mixtures of nucleic acids (e.g., RNA and DNA, both naturally occurring nucleic acids, synthesized nucleic acids, mutant nucleic acids, and recombinant nucleic acids) or lipids (e.g., membranes or membrane fragments). In one embodiment, the target is involved in a disease state of interest. Furthermore, it may be necessary to vary the conditions such that the target is able to maintain its cellular configuration.

The screening assays can be conducted in a variety of ways. For example, one method for identifying small molecules that interact with a target or targets involves anchoring a target onto a solid phase, contacting it with samples of small molecules, and detecting target/sample complexes anchored on the solid phase at the end of the reaction.

For example, microtiter plates may be used as the solid phase. The anchored component may be immobilized by non-covalent or covalent attachments. Non-covalent attachment may be accomplished by simply coating the solid surface with a solution of the sample or the target and drying. The surfaces may be prepared in advance and stored. Covalent attachments include, for example, chemically linking the compound or target to the plate.

In one method of conducting the assay, the nonimmobilized component is added to the coated surface containing the anchored component. After the reaction is complete, unreacted components are removed under conditions such that any target-sample complexes formed are capable of being detected. The complexes may be anchored on to the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

In another embodiment, the invention provides a method (also referred to herein as a "screening assay") for identifying targets which bind to the samples of the library. It also includes methods for identifying samples of the library which have a stimulatory or inhibitory effect on targets, for example, or target activity.

In an embodiment, the invention provides assays for screening libraries of the invention to identify samples which bind to or modulate the activity of a target. Libraries of samples may be presented in solution (e.g., Houghten (1992) *Biotechniques* 13:412–421), on beads (Lam (1991) *Nature* 354:82–84), or chips (Fodor (1993) *Nature* 364: 555–556).

For example, in one embodiment, the samples are prepared appropriately for a interaction with a specific target using a high thoroughput screen. The high throughput screen then is used to identify which of the samples, bind or otherwise interact with the target.

In one embodiment, an assay is a cell-based assay in which a cell which expresses a target (e.g., a protein of interest or a biologically active portion thereof) is contacted with a sample of the library and the ability of the sample to modulate the target's activity is determined. Determining the ability of the sample to modulate the target's activity can be accomplished by methods suitable for the particular target. Determining the ability of the sample to modulate the ability of a target to bind to its substrate can be accomplished, for example, by coupling the substrate with a radioisotope or enzymatic label such that binding of the target to its substrate can be determined by detecting the labeled substrate in a complex with the target. For example, substrates can be labeled with $^{125}I$, $^{35}S$, $^{14}C$, or $^{3}H$, either directly or indirectly, and the radioisotope detected by direct counting of radioemmission or by scintillation counting. Alternatively, substrates can be enzymatically labeled with, for example, horseradish peroxidase, alkaline phosphatase, or luciferase, and the enzymatic label detected by determination of conversion of an appropriate substrate to product.

In another embodiment, an assay is a cell-based assay comprising contacting a cell expressing a target substrate with the samples of the invention and determining the ability of the samples to modulate (e.g., stimulate or inhibit) the activity of the target.

Determining the ability of a target to bind to or interact with a target substrate can be accomplished by one of the methods described above for determining direct binding. In an embodiment, determining the ability of the target to bind to or interact with its substrate can be accomplished by determining the activity of the substrate. For example, the activity of the substrate can be determined by detecting induction of a cellular second messenger of the target, detecting catalytic/enzymatic activity of the target or its substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a target (e.g., a protein, a polypeptide, or a nucleic acid) is contacted with a sample of the invention and the ability of the samples to bind to the target is determined. Binding of a sample to the target can be determined either directly or indirectly as described above. In a further embodiment, the assay includes contacting the target with a compound which is known to bind to the target to form an assay mixture, contacting the assay mixture with a sample of the invention, and determining the ability of the sample to interact with the target, wherein determining the ability of the sample to interact with the target comprises determining the ability of the sample to preferentially bind to the target as compared to the known compound.

In another embodiment, the assay is a cell-free assay in which a target is contacted with a library of compounds of the invention and the ability of the compounds to modulate (e.g., stimulate or inhibit) the activity of the target is determined. Determining the ability of the test compound to modulate the activity of the target can be accomplished, for example, by determining the ability of the target to bind to another molecule by one of the methods described above for determining direct binding. Determining the ability of the target to bind to another molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting the target with a compound which is known to bind to the target to form an assay mixture, contacting the assay mixture with a sample of the invention, and determining the ability of the sample to interact with the target, wherein determining the ability of the sample to interact with the target comprises determining the ability of the sample to preferentially bind to or modulate the activity of the target.

The libraries of compounds of the invention can also be screened using combinatorial methods such as those described in WO 99/31267 for the simultaneous identification of novel biological targets and lead structures for drug development.

14. Small Molecules Databases and Methods of Use

In one embodiment, the invention pertains to the creation of small molecule databases containing information regarding the metabolome of cells, cellular compartments, and organelles, e.g., cells, cellular compartments, and organelles in health, diseased, and altered states. The information regarding the small molecules of each cell, cellular compartment, or organelle can be found using the separation and analytical techniques described elsewhere in the application. The small molecule databases can include compounds derived from the same or different animal organs. For example, the small molecule databases can include compounds obtained from cells of specific organs such as a heart, brain, kidney, liver, done, blood, gastrointestinal tract, and/or muscle. In addition, the small molecule databases can include information regarding compounds obtained from individuals suffering from a particular disease state, e.g., cardiovascular diseases, neurodegenerative diseases, diabetes, obesity, immunological disorders, etc.

The databases can be made based on information obtained from the techniques described elsewhere in the application to determine the identity and presence of various small molecules in cells, cellular compartments, and organelles. The databases may include information regarding the compounds found, such as structure, molecular weight, amounts found in particular organelles in a particular state of health, and any other information that a person of skill in the art would consider relevant and useful to be contained in the database. For example, information regarding known biochemical pathways involving the particular compound may also be included as well as other such information.

In one embodiment, the databases of the invention contain information on the compounds of the metabolome of a particular organelle of a particular species in a particular state of health from a particular organ (e.g., one database may include compounds of the metabolome of the mitochondria of a healthy human heart). In other embodiments, the databases may include information regarding the metabolome of a variety of organelles (e.g., mitochondria, nuclei, Golgi apparatus, endoplasmic reticulum, ribosomes, cytosol, chloroplasts, etc.) or cells from a particular species from a particular organ in a particular state of health. In another embodiment, the databases may include information regarding either specific organelles or cells from a variety of tissues (e.g., fatty tissue, muscle tissue, nerve tissue, brain tissue, heart tissue, bone tissue, blood, connective tissue, retinal tissue, etc.) from an organism in a health or diseased stated (e.g., the tissue can be from an organism suffering from any disorder known to afflict it). Examples of disorders include neurological disorders, central nervous system disorders, metabolic disorders, cardiovascular disorders, immunological disorders, oncological disorders. In a further embodiment, a database may comprise information regarding compounds of the entire metabolome of a particular species, e.g., human, rat, mouse, dog, cat, etc.

If the database is in electronic form, the program used to organize the database can be any program known in the art which is capable of storing the information in a useful format.

The databases of the invention can be organized in such a way that they can be licensed to companies, such as pharmaceutical companies. The databases can then be used for many purposes, such as drug discovery, design, etc.

14. Methods of Identifying Biologically Active or Disease Relevant Small Molecules from Cell Samples In one embodiment, the invention pertains to yet another method for identifying biologically active small molecules. This method includes obtaining cells from a tissue culture or an animal source; obtaining samples of small molecules; testing the samples for biological activity; and identifying samples which have biological activity. The samples that are found to have biological activity can then be further fractionated and profiled by methods known in the art, such as HPLC, thin layer chromatography (TLC), and electrochemical methods. The resulting compounds or fractions can then be retested for biological activity. If desired, the fractionation can continue until the individual compounds or mixtures of compounds with biological activity are identified. These biologically active compounds can then be used, for example, as lead compounds for drug design, used as pharmaceutical or nutriceutical agents, labeled and used to identify other components of pathways associated it, or used in other advantageous capacities.

The term "tissue culture or source" includes subjects, such as plants, bacteria, prokaryotes, eukaryotes, animals (e.g., yeast, mammals, e.g., rats, mice, dogs, cats, primates (e.g., humans, chimpanzees, monkeys), horses, cattle, and bears). The subjects may be healthy, suffering from a disease state, or at risk of suffering from a disease state. Examples of disease states include those which alter the amounts of various small molecules of the cell or cellular compartment (e.g., diabetes, cancer, AIDS, neurodegenerative disorders, etc.). The language "tissue culture or source" includes cell lines such as can be found deposited with ATCC (e.g., cell lines corresponding to disease states, bacterial cell lines, animal cell lines, etc.). If necessary, the cells can be cultured according to methods and techniques known in the art (see, for example, Ausubel et al. *Current Protocols in Molecular Biology* (N.Y.: John Wiley & Sons). Other examples of sources include, for example, cells from CAP23, Hela, human cell cultures, human placenta, lymphoblasts, mammalian muscle biopsies, rat brain, rat liver, and yeast.

In one embodiment, the samples are test fractions, fractionated by techniques known in the art, such as, for example, HPLC (Kristal, et al. *Anal. Biochem.* 263:18–25 (1998)), thin layer chromatography (TLC), or other methods known in the art (*Methods of Enzymology*). The test fractions may be separated based on molecular weight. The test fractions can then be screened for biological activity, before, after, or without further purification. The biologically active samples or test fractions can then be further fractionated and characterized using methods such as, for example, mass spectroscopy (Teusink, B. et al. *Methods Microbiol.*, 26: 297–336 (1998)), infra-red spectroscopy, and nuclear magnetic resource (Brindle, K. et al. *J. Mol. Recog.* 10:182–187 (1997)) to identify biologically active small molecules.

The term "biologically active small molecules" include small molecules which modulate the activity of a biological system or pathway. For example, biologically active small molecules may be identified using in vitro or in vivo assays known in the art. Biologically active small molecules can also be identified by screening assays against protein targets which have been implicated in a disease state. In another embodiment, biologically active small molecules can be identified using cell-based assays. For example, biologically active small molecules with anti-tumor activity can be identified, for example, by their effect on the growth of a panel of tumor cell lines (Lillie et al. *Cancer Res.* 53(13): 3172–8 (1993)). Similarly, biologically active small molecules with neuronal protection activity may be identified by exposing primary or cultured neurons to the compounds and toxic agents, such as glutamate, and identifying the compounds which protect the neurons from death. Animal models can also be used to identify biologically active small molecules. For example, animal models of Huntington's Disease, Parkinson's disease, and ALS can be used to identify biologically active small molecules useful as neuroprotective agents. (Kilvenyi, *Nature Med.* 5:347–350 (1999); Mathews et al, *Experimental Neurology* 157:142–149 (1999)). In a further embodiment, the identified biologically active small molecules can then be chemically modified to further enhance their pharmaceutical or nutriceutical properties.

The term "isolated" includes molecules (e.g., small molecules) which are separated from other molecules which are present in the natural source of the molecules. In an embodiment, an "isolated" small molecule is free of other molecules (both other small molecules and macromolecules) which naturally are present of the organism from which the small molecules are derived.

15. Use of Small Molecule Profiles for Tissue Typing and Forensic Science

The small molecule profiling of cells, cellular compartments, and/or particular organelles of the present invention can also be used to identify individuals from minute biological samples. The method includes taking one or more samples from a subject and determining the small molecule profiles of the samples; taking a sample from a unknown source and determining its small molecule profile; and comparing the two small molecule profiles to determine whether the small molecule profiles are from the same individual.

It is expected that certain small molecules will be present in unique amounts in each person's cells, cellular compartments, or organelles. By using several of these compounds as markers, one could determine whether or not a sample was or was not obtained from the same individual as a reference sample. This method of tissue typing can be used alone or in combination with more conventional techniques for determining the source of a tissue sample. Examples of conventional techniques include RFLP (restriction fragment length polymorphism, U.S. Pat. No. 5,272,057), DNA analysis (e.g., PCR), blood typing, etc.

In addition, a database can be created out of numerous individuals' small molecule profile, thus enabling the positive identification of even a small tissue sample whose small molecule profile is registered with the database.

Small molecule profiling of cells and cellular organelles can also be used in forensics. Forensic biology is a scientific field employing, for example, genetic typing of biological evidence found at a crime scene as a means for positively identifying a perpetrator of a crime. In traditional DNA-based forensics, PCR technology is used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

It is believed that the small molecule profile of each person's body fluids, cells, or cellular organelles, should contain unique amounts of various small molecule. Therefore, a small molecule profile of a given sample should yield a unique "fingerprint" of the perpetrator of the crime. Unlike conventional techniques, the present invention allows for a quick profile of the sample without the time consuming task of PCR. PCR is dependent on a multitude of repeated copies of the perpetrator's DNA, and therefore, its reliability is somewhat uncertain. The invention also encompasses methods for using the claimed small molecule profiles in combination with more conventional techniques, such as PCR, for enhanced sensitivity.

The small molecule profiles of the invention can also be used to develop small molecule reagents to identify particular tissue types. For example, certain tissues (e.g., muscle, nervous tissue, fatty tissue, etc.) should have unique small molecule profiles as compared to other body tissues. These tissues will have enhanced concentrations of certain key small molecules and have diminished concentrations of others. The identity of these tissue specific small molecules may be consistent over a subset of the population or the entire species as a whole.

Therefore, the invention pertains to the use of small molecule reagents that specifically react with key small molecules identified as being localized to a specific tissue over a subset of the population. The small molecule reagents can then be used to identify the identity of a tissue of unknown origin (e.g., brain, muscle, fatty tissue, etc.).

16. Pharmaceutical Compositions

In another embodiment, the invention pertains to pharmaceutical compositions comprising a biologically active small molecule, disease relevant, or another molecule obtained through using the methods of the invention and a pharmaceutically acceptable carrier. In another embodiment, the invention includes nutriceutical preparations of biologically active small molecules of the invention.

The biologically active small molecules may be chemically modified to enhance their biological activity. It is known in the art that through chemical modifications, one can enhance the biological activity, stability, or otherwise modify a molecule to make it more suitable as a pharmaceutical or nutriceutical agent.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

This invention is further illustrated by the following examples which should not be construed as limiting. The contents of all references and published patents and patent applications cited throughout the application are hereby incorporated by reference.

17. Agricultural Methods of the Invention

In another embodiment of the invention, the invention includes a method for the identification of agents useful for agriculture, such as for example, insecticides, pesticides, herbicides, and fertilizers.

Plants are an excellent source of small molecules. Many plant small molecules have been shown to have therapeutic benefit. Therefore, in one embodiment, the invention pertains to a library of the small molecules from plant extracts (e.g., extracts from a particular plant or part of plant (e.g., seeds, flowers, berries, roots, sap, leaves, etc.), cells from the plant, organelles (e.g., mitochondria, chloroplasts, nuclei, Golgi apparatus, etc.), cellular compartments, etc. These libraries can also be screened for biologically active molecules using the methods described in previous sections. Furthermore, the plants also can be analyzed using any of the separation or analytical techniques described herein, e.g., HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art.

Furthermore, comparison of plant small molecule profiles could lead to the identification of compounds which are relevant to the plant's resistance of certain diseases or environmental conditions.

In addition, the method also pertains to small molecule profiles and small molecule libraries of plants. For example, the small molecule profiles can be used to determine plant deficiencies of certain compounds, and analyze plant diseases in a method analogous to the comparison of animal small molecule profiles. For example, a small molecule profile can be determined of a specific plant cell, cell compartment or organelle (e.g., chloroplast, mitochondria, endoplasmic reticulum, Golgi apparatus, etc.). Standard plant cell profiles can also be generated. These can be compared to plants in particular disease states to determine which small molecules are present in aberrant amounts in the diseased cells.

In one method of the invention, small molecule profiles of insect cells, cellular compartments, or specific organelles are compared to small molecule profiles of insect cells, cellular compartments, or organelles treated with a known insecticide. The small molecule profiles can be compared to identify compounds which are relevant to the insecticide activity. The compounds which are identified as relevant can then be identified to further optimize the insecticidal activity of the compounds.

The term "insecticides" include compounds which kill or other wise limit the reproductive capacity of organisms from the order Isopoda (e.g., *Oniscus asellus, Armadillidium vulgare* and *Porcellio scaber*, the order Diplopoda (e.g., *Blaniulus guttulatus*), the order Chilopoda (e.g., *Geophilus carpophagus, Scutigera* spec, etc.), the order Symphyla (e.g., *Scutigerella immaculata*, etc.), the order Thysanura (e.g., *Lepisma saccharina*, the order Collembola (e.g., *Onychiurus armatus*), the order Orthoptera (e.g., *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria*, etc.), the order Dermaptera (e.g., *Forficula auricularia*, etc.), the order Isoptera (e.g., *Reticulitermes* spp, etc.), the order *Anoplura* (e.g., *Pediculus humanus corporis, Haematopinus* spp., *Linognathus* spp. etc.), the order Mallophaga (e.g., *Trichodectes* spp. *Damalinea* spp., etc.), the order Thysanoptera (e.g., *Hercinothrips femoralis, Thrips tabaci*), the order Heteroptera (*Eurygaster* spp., *Dysdercus intermedius, Piesma quadrata, Cimex lectularius, Rhodnius prolixus* and *Triatoma* spp., etc.), the order Homoptera (e.g., *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Phylloxera vastatrix, Pemphigus* spp., *Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp., etc.), the order Lepidoptera, (e.g., *Pectinophora gossypiella, Bupalus piniarius, Cheimatobia brumata, Lithocolletis blancardelia, Hyponomeuta padella, Plutella maculipennis, Malacosoma neustria, Euproctis chrysorrhoea, Lymantria* spp. *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana*, etc.), the order Coleoptera (e.g., *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis Costelytra zealandica*, etc.), the order Hymenoptera, (*Diprion* spp., *Hoplocampa* spp., *Lasius* spp., *Monomorium pharaonis, Vespa* spp., etc.), the order of the Diptera (e.g., *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa*, etc.), the order Siphonaptera (e.g., *Xenopsylla cheopis* and *Ceratophyllus* spp., etc.), the order Arachnida (e.g., *Scorpio maurus, Latrodectus mactans*, etc.), the order Acarina (e.g., *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp, etc.), *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., and *Trichodorus*; spp.

In another embodiment, small molecule profiles of insect cells treated with a test compound can be compared to small molecule profiles of insect cells treated with a known insecticide to determine whether the test compound may be an active insecticide.

The invention also pertains to insecticides comprising one or more insecticides identified by the methods of the invention. In one embodiment, the insecticides of the invention are non-toxic to humans.

The insecticide compositions of the invention, both solids and liquids, may be applied to insect infestations or insect populations by spraying. The methods and equipment needed for a given treatment may be determined by one skilled in the art. Furthermore, methods of the invention described herein may be used to treat insect infestations or populations in dry, moist, or aquatic systems (e.g., the insect-infested area is a flowing or a standing body of water). An aquatic system which is treated with methods of the present invention may be either fresh water or salt water. Furthermore, the insect control compositions of the invention may be applied directly onto a host (e.g., an agricultural crop, a turfgrass).

EXEMPLIFICATION OF THE INVENTION

Example 1

Method for Obtaining a Small Molecule Profile of a Cellular Compartment

Method for Obtaining a Small Molecule Profile of Mitochondria Using HPLC

The following method demonstrates how small molecules are isolated from mitochondria for methods as described herein.

Mitochondrial Isolation

Mitochondria from a mammalian source are isolated by differential centrifugation in 140 mM KCl and 20 mM Hepes, pH 7.4. Following the final wash, mitochondria are resuspended in the same buffer and aliquots are quick frozen in liquid nitrogen. Protein determinations are carried out by Lowry using the Sigma Protein Assay Kit P5656).

Other mitochondrial samples are purified using a modified version of a published protocol (Rigobello et al. (1995) *Arch. Biochem. Biophys.* 319, 225–230). Mammalian liver mitochondria are obtained after decapitation of the subjects. The livers are dissected out and are placed in an ice-cold solution containing 250 mM mannitol, 75 mM sucrose, 100 $\mu$M EDTA, 500 $\mu$M EGTA, and 10 mM Hepes (pH 7.4). The livers are homogenized with a motor-driven Teflon pestle and the homogenate is centrifuged at 1000 g for 10 min. Supernatants are removed and centrifuged at 10,000 g for 15 min. The pellets are washed in 250 mM mannitol, 75 mM sucrose, 100 $\mu$M EDTA, 500 $\mu$M EGTA, and 10 mM Hepes (pH 7.4) with 0.5% bovine serum albumin (BSA) (Sigma A-6003). Following centrifugation, the pellets are then washed twice more in 250 mM mannitol, 75 mM sucrose, 30 $\mu$M EDTA, and 10 mM Hepes (pH 7.4) with 0.5% BSA. Following the final wash, mitochondria are resuspended in the 5 ml of the final buffer without BSA. An aliquot is removed, pelleted in a microfuge, washed once with 160 mM KCl, repelleted, and dry-frozen at −80° C. Samples are analyzed by HPLC within 1 week of isolation.

HPLC Standards

Basic HPLC and Coulometric array methodology has been previously described with regard to their use for serum, urine, and tissue analysis (Beal et al. (1990) *J. Neurochem.* 55:1327; Matson et al. (1987) *Life Sci.* 41:905; LeWitt et al. (1992) *Neurology* 42:2111; Ogawa et al. (1992) *Neurology* 42:1702; Beal et al. (1992) *J. Neurol. Sci.* 108:80). Standards for stock solutions are obtained from Sigma and stored at −80° C. as 1 mg/ml stocks in 20% MeOH containing 1% phosphoric acid. Subsequent dilution to working strength is made into 0.1 M NaCl. The assay sequence is: standard, 8 samples, sample pool, standard, etc. Within-run precision is derived from the prevision of the repeated pool assays. Precision varies primarily as a function of the level of the analyte and secondarily as the complexity of the region in which it occurs. Typically at 5 pg precision is ±20%, at 500 pg ±5%, and at 1 ng ±3%.

Sample Preparation

Mitochondrial samples, including approximately 5 mg of mitochondrial protein, are precipitated and extracted in 4 vol of acetonitrile, 4% acetic acid at −20° C. One milliliter of centrifuged supernatant is removed, evaporated to dryness under vacuum, and reconstituted in 200 $\mu$l of mobile phase A (11 g/liter of pentane sulfonic acid at pH 3.00 with acetic acid). Recoveries, verified by sequential extractions and comparisons of entire patterns, ranged from 93 to 100% for all compounds resolved. This protocol conserves reactive species such as ascorbate and homogentistic acid at 1 ng/ml concentrations. Reconstituted extract equivalent to 2 mg of mitochondrial protein is placed in an auto sample vial and immediately analyzed. Remaining extract is frozen at −80° C. for future confirmation analysis. Immediately prior to injection, samples are maintained in an autoinjector at 0–1° C.

Chromatographic Methods

To retain stability of retention times and response potentials, a mobile phase combination of mobile phase A (above) and mobile phase B (0.1 M Li-acetate at pH 3.00 with acetic acid in 80/10/10 methanol/acetonitrile/isopropanol) is used. The chromatographic method involves a 120-min complex gradient from 0% B to 100% B, with flow rate adjusted to compensate for aziotropic viscosity effects, and has been previously described in detail (Milbury et al. (1997) in *Progress in HPLC, Coulometric Electrode Array Detectors for HPLC*, pp. 125–141, VSP International Science Publications). The mixed gradient is delivered from a peak suppressor/gradient mixer to a PEEK-lined pulse damper prior to flowing through the auto sampler injector and on to two series C18 columns [META250, 5-$\mu$m ODS, 250×4.6 mm I.D., ESA, Inc.].

The small molecules are detected using a 16-channel coulometric electrode array (ESA, Inc., Model 5600 CEAS gradient system equipped with a Kontron Model 460 autosampler) incremented from 0 to 900 mV in 60-mV steps. Peak suppressor/gradient mixer, pulse damper, columns, and detectors are contained within a temperature-controlled enclosure maintained at 35° C. System functions are controlled by 5600-CEAS software installed on a 386 microcomputer.

The detected small molecules can then be analyzed on a computer to create a small molecule profile. The small molecule profile can then be compared, e.g., via subtraction, with small molecule profiles of other samples. The isolated small molecules can then be used in assays known in the art to determine biological activity.

Example 2

Method for Analyzing Metabolic Disorders Using Small Molecule Profiles

Method for Analyzing Differences in Small Molecule Profiles of Genetically Altered Mice After Short Term Diet Variations 15 female C57B1/6J ob/ob mice and lean littermate controls (15 female C57B1/6J ?/+) and 15 male C57B1/Ks db/db mice and lean littermate controls (15 male C57B1/ks +/+) are obtained from Jackson labs at 4.5 weeks of age, and are housed individually on normal mouse chow (West, D. B., 1992, *Am. J. Physiol.* 262:R1025-R1032) for 1 week prior to the initiation of the study. The four groups of 15 mice each are then sacrificed by $CO_2$ euthanasia and tissues are then collected. Body weight (grams) of the four groups of mice at the time of sacrifice are measured. Small molecule profiles from cells from the hypothallumus are then obtained from each group of mice and compared.

The mice (normal, lean, ob/ob, db/db, and/or tub/tub) are fed normally prior to the initiation of the experiment, and then they are divided into one control and two experimental groups. The control group are then maintained on ad lib nourishment, while the first experimental group ("fasted group") is fasted, and the second experimental group ("fasted-refed group") is initially fasted, and then offered a highly palatable meal shortly before the collection of tissue samples for small molecule profiling. Each test animal is weighed immediately prior to and immediately after the experiment. Small molecule profiles are taken of each mouse from each group before and after the experiment. The profiles of each group are averaged and compared to those of different groups.

Method for Comparing Small Molecule Profiles of Mice After Long Term Diet Variations Mice are fed normally prior to the initiation of the experiment, and then are divided into one control and two experimental groups. The control group is then maintained on an ad lib diet of normal nourishment in order to calculate daily food intake. The first experimental group ("underweight group") is then underfed by receiving some fraction of normal food intake, 60–90% of normal, for example, so as to reduce and maintain the group's body weight to some percentage, for example 80%, of the control group. The second experimental group ("overweight group") is overfed by receiving a diet which would bring the group to some level above that of the control, for example 125% of the control group. Tissue samples are obtained for small molecule profiles to determine compounds which are present in different amounts in control versus overweight and/or underweight conditions.

Example 3

Comparison of Small Molecule Profiles of Different Types of Immune Cells

Method for Comparing the Small Molecule Profiles of TH1 and TH2 Cells

The transgenic T cell example is used to identify cellular small molecules present in TH2 cells. The identified small molecules are be present in different amounts in TH2 cells compared to TH1 cells.

Transgenic Mice

Naive $CD4^+$ cells are obtained from the spleens and/or lymph nodes of unprimed transgenic mouse strains harboring a T cell receptor (TCR) recognizing ovalbumin (Murphy et al., 1990, *Science* 250:1720).

Ova-Specific Transgenic T Cells

Suspensions of ova-specific T cells are co-cultured with stimulatory peptide antigen and antigen presenting cells essentially as described in Murphy et al. (Murphy et al., 1990, *Science* 250:1720). Briefly, 2–4×10⁶ T cells are incubated with approximately twice as many TA3 antigen presenting cells in the presence of 0.3 $\mu$M Ova peptide. TH1 cultures may contain approximately 10 ng/ml recombinant mIL-12. Conversely, TH2 cells received IL-4 (1000 $\mu$/ml). Cultures are harvested at various time points after initiation of culture. T cells are purified of TA3 cells using anti-CD4 coated magnetic beads (Dynal, Inc.). T cells are then pelleted by gentle centrifugation and lysed.

Tissue Collection:

Cells are then quick frozen on dry ice. Samples are homogenized together with a mortar and pestle under liquid nitrogen.

Mitochondrial Isolation and Generation of Small Molecule Profiles

Cellular mitochondria are isolated and small molecule profiles are generated using the procedure given in Example 1.

Method for Comparing Small Molecule Profiles of Different TH Cell Subpopulations In this Example, the generation of small molecule profiles representing small molecules which are present in different amounts in TH cell subpopulations and/or during the differentiation of such subpopulations are described.

TH cell clones such as, D10.G4 (TH2), AE7 (TH1) and D1.1 (TH1), are used. Prior to stimulation, cell cultures are enriched for live cells by centrifugation through a Ficoll gradient. Recovered cells are then counted and their viability is examined using trypan blue exclusion. Cells are replated into either T25 or T75 flasks at approximately $5\times10^6$ cells in 5 mLs or $1.5\times10^6$ cells in 10 mLs of culture medium, respectively.

Coating is then performed, generally, according to Current Protocols in Immunology, 1992, Coligan, J. E. et al., John Wiley & Sons, NY, pp 3.12.4–3.12.6). Specifically, prior to plating, the flasks are coated with anti-CD3-ε antibodies (hybridoma supernatant from the 145-C11 hybridoma; Parmingen, Inc., San Diego Calif.). For coating, antibodies are resuspended in PBS at 1–2 $\mu$g/ml at a volume sufficient to coat the bottom of the flasks. Coating solution is incubated on the flasks for at least one hour at 37° C.

After incubation, the antibody coating solution is removed by aspiration and cells will be immediately added. Flasks will then be placed in a 37° C. incubator for 6 hours.

Cells are harvested by, for example, removal of supernatant from the culture. The mitochondria are removed from the cells by the procedure given above. Small molecule profiles of each type of TH cell can then be done and analyzed to determine differences and similarities between the subpopulations.

Example 5

Method of Identifying Cardiovascular Disease Relevant Small Molecules

Method Using an Endolethial Cell Shear Stress Models to Obtain Small Molecule Profiles and Identify Disease Relevant Small Molecules Cell Culture Primary cultures of HUVEC's are established from normal term umbilical cords as described (*In Progress in Hemostasis and Thrombosis*, Vol. 3, P. Spaet, editor, Grune & Stratton Inc., New York, 1–28). Cells are grown in 20% fetal calf serum complete media (1989, J. Immunol. 142: 2257–2263) and passaged 1–3 times before shear stress induction.

For induction, second passage HUVEC's are plated on tissue culture-treated polystyrene and subjected to 10 dyn/cm.sup.2 laminar flow for 1 and 6 hr. as described (1994, J. Clin. Invest. 94: 885–891) or 3–10 dyn/cm$^2$ turbulent flow as previously described (1986 Proc. Natl. Acad. Sci. U.S.A. 83: 2114–2117).

Mitochondrial Isolation

Mitochondria from the HUVEC's are isolated by differential centrifugation in 140 mM KCI and 20 mM Hepes, pH 7.4. Following the final wash, mitochondria are resuspended in the same buffer and aliquots are quick frozen in liquid nitrogen. Protein determinations are carried out by Lowry using the Sigma Protein Assay Kit P5656).

Sample Preparation

Mitochondrial samples, including approximately 5 mg of mitochondrial protein, are precipitated and extracted in 4 vol of acetonitrile, 4% acetic acid at −20° C. One milliliter of centrifuged supernatant is removed, evaporated to dryness under vacuum, and reconstituted in 200 µl of mobile phase A (11 g/liter of pentane sulfonic acid at pH 3.00 with acetic acid). Reconstituted extract equivalent to 2 mg of mitochondrial protein is placed in an auto sample vial and immediately analyzed. Immediately prior to injection, samples are maintained in an autoinjector at 0–1° C.

Chromatographic Methods

To retain stability of retention times and response potentials, a mobile phase combination of mobile phase A (above) and mobile phase B (0.1 M Li-acetate at pH 3.00 with acetic acid in 80/10/10 methanol/acetonitrile/isopropanol) is used. The chromatographic method involves a 120-min complex gradient from 0% B to 100% B, with flow rate adjusted to compensate for aziotropic viscosity effects, and has been previously described in detail (Milbury et al. (1997) in *Progress in HPLC, Coulometic Electrode Array Detectors for HPLC*, pp. 125–141, VSP International Science Publications). The mixed gradient is delivered from a peak suppressor/gradient mixer to a PEEK-lined pulse damper prior to flowing through the auto sampler injector and on to two series C18 columns [META250, 5-µm ODS, 250×4.6 mm I.D., ESA, Inc.].

The small molecules are detected using a 16-channel coulometric electrode array (ESA, Inc., Model 5600 CEAS gradient system equipped with a Kontron Model 460 autosampler) incremented from 0 to 900 mV in 60-mV steps. Peak suppressor/gradient mixer, pulse damper, columns, and detectors are contained within a temperature-controlled enclosure maintained at 35° C. System functions are controlled by 5600-CEAS software installed on a 386 microcomputer.

The detected small molecules can then be analyzed on a computer to create a small molecule profiles. The small molecule profiles of the cells are then compared to those not subjected to the turbulent flow. Small molecule present in aberrant amounts in the sample subjected to the turbulent flow are identified for further investigation.

Example 6

Identification of Disease Relevant Small Molecules in Human Cell Samples

Human Tumor Example

In this example, a cell sample is taken from a malignant tumor in a human subject. Normal tissue is also collected from the subject from the same or similar tissue as the tumor (e.g., normal breast tissue and breast tumor tissue; normal prostate tissue and prostate tumor tissue, etc.). Normal tissue is also collected from a healthy subject from an analogous tissue location.

The tissue samples are the homogenized and the mitochondria are isolated.

Mitochondrial Isolation

Mitochondria from a each tissue source are isolated by differential centrifugation in 140 mM KCI and 20 mM Hepes, pH 7.4. Following the final wash, mitochondria are resuspended in the same buffer and aliquots are quick frozen in liquid nitrogen. Protein determinations are carried out by Lowry using the Sigma Protein Assay Kit P5656).

Sample Preparation

The mitochondrial samples, including approximately 5 mg of mitochondrial protein, are precipitated and extracted in 4 vol of acetonitrile, 4% acetic acid at −20° C. One milliliter of centrifuged supernatant is removed, evaporated to dryness under vacuum, and reconstituted in 200 µl of mobile phase A (11 g/liter of pentane sulfonic acid at pH 3.00 with acetic acid). Reconstituted extract equivalent to 2 mg of mitochondrial protein is placed in an auto sample vial and immediately analyzed. Immediately prior to injection, samples are maintained in an autoinjector at 0–1° C.

Chromatographic Methods

To retain stability of retention times and response potentials, a mobile phase combination of mobile phase A (above) and mobile phase B (0.1 M Li-acetate at pH 3.00 with acetic acid in 80/10/10 methanol/acetonitrile/isopropanol) is used. The chromatographic method involves a 120-min complex gradient from 0% B to 100% B, with flow rate adjusted to compensate for aziotropic viscosity effects, and has been previously described in detail (Milbury et al. (1997) in *Progress in HPLC, Coulometic Electrode Array Detectors for HPLC*, pp. 125–141, VSP International Science Publications). The mixed gradient is delivered from a peak suppressor/gradient mixer to a PEEK-lined pulse damper prior to flowing through the auto sampler injector and on to two series C18 columns [META250, 5-µm ODS, 250×4.6 mm I.D., ESA, Inc.].

The small molecules are detected using a 16-channel coulometric electrode array (ESA, Inc., Model 5600 CEAS gradient system equipped with a Kontron Model 460 autosampler) incremented from 0 to 900 mV in 60-mV steps. Peak suppressor/gradient mixer, pulse damper, columns, and detectors are contained within a temperature-controlled enclosure maintained at 35° C. System functions are controlled by 5600-CEAS software installed on a 386 microcomputer.

Analysis

The small molecule profiles of the healthy subject are compared to the small molecule profiles from the tumor tissue and the non-tumor tissue of the cancer patient. Small molecules which are present in aberrant amount in the tumor tissue are identified by comparing the profiles.

INCORPORATION BY REFERENCE

The entire contents of all references and patents cited herein are hereby incorporated by reference. The entire contents of U.S. Pat. No. 5,908,609 and all its references also expressly incorporated herein.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for identifying small molecules relevant to amyotrophic lateral sclerosis, comprising:
   obtaining a small molecule profile of a sample from a subject suffering from amyotrophic lateral sclerosis; and
   identifying the small molecules relevant to amyotrophic lateral sclerosis using the small molecule profile, wherein said small molecule profile is obtained using one or more techniques which detect 50% or more of the small molecules in said sample.

2. A method for identifying small molecules relevant to amyotrophic lateral sclerosis, comprising:
   obtaining a small molecule profile of a subject sufering from amyotrophic lateral sclerosis; and
   identifying the small molecules relevant to said nervous system disorder using the small molecule profile, wherein the small molecule profile is obtained using one or more techniques which detect 50% or more of the small molecules in the sample and,
   wherein said small molecule profile comprises information regarding the presence of two or more types of small molecules selected from the group consisting of: sugars, fatty acids, amino acids, nucleotides, metabolites, and products of catabolism.

3. The method of claim 1 or 2, wherein said subject is a human.

4. The method of claim 1 or 2, wherein said small molecule profiles are obtained from said subject's blood, spinal fluid, serum, cells, tissue or cellular organelles.

5. The method of claim 1 or 2, wherein said small molecule profiles are obtained using one of more of the following: HPLC, TLC, electrochemical analysis, mass spectroscopy, refractive index spectroscopy (RI), Ultra-Violet spectroscopy (UV), fluorescence analysis, radiochemical analysis, Near-Infra Red spectroscopy (Near-IR), Nuclear Magnetic Resonance (NMR) and Light Scattering analysis (LS).

* * * * *